United States Patent [19]
Klaveness et al.

[11] Patent Number: 5,534,250
[45] Date of Patent: Jul. 9, 1996

[54] POLYMERS CONTAINING DIESTER UNITS

[75] Inventors: Jo Klaveness; Per Strande, both of Oslo; Unni N. Wiggen, Rasta, all of Norway

[73] Assignee: Nycomed Imaging AS, Oslo, Norway

[21] Appl. No.: 982,746

[22] PCT Filed: Sep. 7, 1991

[86] PCT No.: PCT/EP91/01751

§ 371 Date: May 5, 1993

§ 102(e) Date: May 5, 1993

[87] PCT Pub. No.: WO92/04392

PCT Pub. Date: Mar. 19, 1992

[30] Foreign Application Priority Data

Sep. 7, 1990 [GB] United Kingdom ............... 9019650
Jul. 8, 1991 [GB] United Kingdom ............... 9114678

[51] Int. Cl.$^6$ ............... A61K 31/765; C08G 63/02; C08G 63/16; C08G 63/48

[52] U.S. Cl. ............... 424/78.37; 525/64; 528/272; 528/302; 528/307; 528/308

[58] Field of Search ............... 424/78.37; 528/272, 528/302, 307, 308; 525/64

[56] References Cited

U.S. PATENT DOCUMENTS 2,341,334 2/1944 Richter ............... 526/321
2,839,572 6/1958 Guest et al. ............... 560/210

FOREIGN PATENT DOCUMENTS 1309105 10/1992 Canada.
2119697 8/1972 France.
1104700 4/1961 Germany.
95108 1/1973 Germany.
3610808 10/1989 Germany.

*Primary Examiner*—Carlos Azpuru
*Attorney, Agent, or Firm*—Bacon & Thomas

[57] ABSTRACT

The present invention relates to biodegradable polymers containing diester units of formula (I)

$$-[CO-O-C(R^1R^2)-O-CO]-$$

where $R^1$ and $R^2$ each represents a hydrogen atom or a carbon-attached monovalent organic group, or $R^1$ and $R^2$ together form a carbon-attached divalent organic group.

13 Claims, No Drawings

POLYMERS CONTAINING DIESTER UNITS

This invention concerns polymers containing optionally substituted methylene diester groupings. Such groupings are capable of being biodegradable since they are labile to common esterase enzymes although in many instances the polymer may remain at least partly intact.

Biodegradable polymers have long been used in the medical field, for example to provide biodegradable implant materials and delayed release drug delivery systems. They are now of wider interest in overcoming the problem of pollution by long-lived insert packaging materials, household articles, detergents and the like.

There is also a need for polymers which, when they wholly or partially break down by chemical or biological means, give reliably non-toxic products.

In general, biodegradation commonly involves enzymic hydrolysis of particular chemical bonds in the polymer, notably ester, urethane or amide groups which are otherwise stable in the absence of enzymes. Thus, for packaging materials, aliphatic polyesters such as polycaprolactone, polyethylene adipate and polyglycolic acid are candidate materials although polyethylene terephthalate, which is very widely used in textiles and fibres, is resistant to biodegradation.

In the medical field, resorbable polymers are of interest for sutures and in wound closure, resorbable implants in the treatment of osteomyelitis and other bone lesions, tissue stapling and mesh tamponades, anastomosis as well as drug delivery systems and diagnostics. In these fields, polylactic acid, polyglycolic acid, poly (L-lactide-co-glycolide), polydioxanone, poly (glycolide-co-trimethylene carbonate), poly (ethylene carbonate), poly (iminocarbonates), polyhydroxybutyrate, poly (amino acids), poly (ester-amides), poly (orthoesters) and poly (anhydrides) have all been proposed (T. H. Barrows, Clinical Materials 1 (1986), pp. 233–257) as well as natural products such as polysaccharides. U.S. Pat. No. 4,180,646, in particular, describes novel poly (orthoesters) for use in a very wide range of products.

However, the polymers hitherto proposed for either medical or more general use have each had one or more disadvantages and there is a demand for alternative polymers, in particular polymers containing readily biodegradable groupings. The present invention is based in the concept that diester units of the formula (I)

$$\{CO-O-C(R^1R^2)-O-CO\}\quad\quad (I)$$

(where $R^1$ and $R^2$ are as defined below) are particularly rapidly degraded by common esterase enzymes but are stable in the absence of enzymes.

A number of polymers containing such units have been described in the prior art. Thus, for example, U.S. Pat. No. 2,341,334 describes the copolymerisation of monomers such as methylidene or ethylidene dimethacrylate with ethylenic monomers such as vinyl acetate, methyl methacrylate or styrene. The resulting copolymers are said to exhibit higher softening points than unmodified homopolymers of the ethylenic monomer and to be useful in the preparation of cast articles. DD-A-95108 and DE-A-1104700 similarly describe the copolymerisation of various alkylidene diacrylate esters with acrylic monomers to yield copolymers with modified physical properties. A number of alkylidene dicrotonates are disclosed in U.S. Pat. No. 2,839,572 as monomers which may be homopolymerised or copolymerised with materials such as vinyl chloride, to yield resins useful as protective coatings. Kimura H. in J. Osaka Univ. Dent. Sch., 20 (1980), pp. 43–49 describes the use of propylidyne trimethacrylate as a crosslinking agent in coating dental polymethylmethacrylate in order to improve its abrasion resistance. Homopolymers of ethylidene, allylidene and benzylidene dimethacrylate are described in FR-A-2119697 and by Arbuzova A. et al. in Zh. Obshch. Khim. 26 (1956), pp. 1275–1277, and typically comprise hard, glassy materials.

EP-A-0052946 discloses the use of certain polyacrylates to stabilise polyhydroxybutyric acid. The only polyacrylate having more than one acryloyloxy group attached to a single carbon atom is pentaerithrityl monohydroxypentaacrylate, which by virtue of its numerous ethylenically unsaturated sites would be expected to form a complex mixture of addition polymers with polyhydroxybutyric acid.

U.S. Pat. No. 3,293,220 describes use of aldehyde dicarboxylates to stabilise polyoxymethylene polymers by acylating the terminal hydroxyl groups. There is no suggestion of cross-linking or incorporation of the aldehyde dicarboxylate residues into the polymer chains.

In such prior art, the diester grouping of formula (I) is introduced into the polymers by polymerisation of an alkylidene diacrylate or dimethacrylate monomer by a free radical mechanism whereby the olefinic bonds polymerise to form polyolefinic chains to which the diester groups are attached in side chains or crosslinking groups. The diester grouping is always of the form in which, referring to formula (I), both carbonyl groups are joined directly to carbon, that is neither of the ester groups is other than a simple carboxylic ester group.

None of this prior art suggests that the diester groupings disclosed therein may be biodegradable; indeed, the introduction of crosslinking groups of the type represented by formula (I) above is generally seen as conveying enhanced rigidity and/or stability.

According to the present invention we have found it possible to prepare novel diester polymers containing linkages of formula (I) above which exhibit high stability in the absence of enzymes, which linkages are degradable by esterases both in the natural environment, e.g. by bacterial attack, and in the human or animal body, to form non-toxic products, even where structural elements of the polymer, e.g. polymer backbone chains, retain their integrity.

In contrast to the diester-containing polyolefinic polymers described in the prior art, which typically are rigidly crosslinked, polymer of the invention may exhibit the property, even when polyolefinic, of being water-swellable. This can convey a number of advantages, for example assisting the ingress of water-borne enzymes into the polymer structure, thereby facilitating biodegraditive attack. Water-swellable polymers may also be treated with aqueous or hydrophilic solutions of, for example, biologically active or diagnostic agents, whereby such agents are incorporated into the polymer. In further embodiments of the invention such agents may also be physically incorporated into the diester polymers during polymerisation or may be covalently bonded either to appropriate monomers which are subsequently polymerised or to preformed polymers.

Thus according to one aspect of the invention we provide polymers containing diester units of the formula (I) where $R^1$ and $R^2$ each represents a hydrogen atom or a carbon-attached monovalent organic group or $R^1$ and $R^2$ together form a carbon-attached divalent organic group, with the proviso that where such units are attached at both ends to carbon atoms and the polymers are polyolefinic, then the polymers are biodegradable and/or are water-swellable and/or are associated with a biologically active or diagnostic agent.

In general, biodegradable polymers are preferred. Polyolefinic polymers have the potential disadvantage of possessing carbon-carbon backbone chains which are not readily degraded although this may not be disadvantageous where the polymers are water-swellable and/or contain biological or diagnostic agents and/or where the polymer backbone chains are water-soluble or dispersible, e.g. after degradation of diester crosslinking groups.

The term 'diester' as used herein refers to the presence of two —CO—O— groups in the units of formula (I). These may be attached not only to carbon-attached organic groups, as in simple carboxylic esters, but to —O— atoms as in carbonate esters.

Thus polymers of the invention may be represented as containing units of the formula (II)

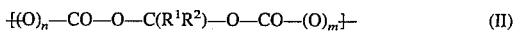

where $R^1$ and $R^2$ are as defined above and m and n, which may be the same or different, are each 0 or 1.

In general, the polymers of the invention will contain units of the formula (III)

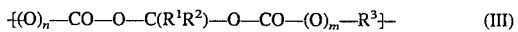

where $R^1$, $R^2$, m and n have the above meanings and $R^1$ is a carbon-attached divalent organic grouping.

The polymers of the invention may advantageously be of relatively low molecular weight, since this may aid both biodegradation and dispersal of the degradation products. Accordingly the term "polymer" as used herein in relation to the invention should be understood to include low molecular weight materials such as oligomers.

Polymers according to the invention may comprise a plurality of units of formula (III) having different meanings for m, n, $R^1$, $R^2$ and $R^3$ for example as in block or graft copolymers. The diester linkages may occur at intervals throughout the polymer, e.g. as crosslinking groups or between copolymer sections, in which case $R^3$ will represent a polymeric grouping. Alternatively the linkages may be present throughout substantially the whole of the polymer, in which case $R^3$ will preferably be a low-molecular grouping.

Particularly interesting units (III) are those in which n is 0 and m is 0 or 1, i.e. dicarboxylate units of the formula (IV)

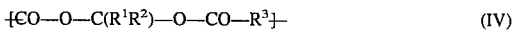

or carboxylate-carbonate units of the formula (V)

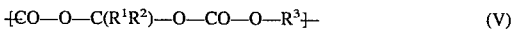

The latter are of particular interest and have not been described previously in polymers of any kind.

$R^1$ and $R^2$ may, for example, each be hydrogen or a carbon-attached hydrocarbyl or heterocyclic group, for example having 1–20 carbon atoms, e.g. an aliphatic group such as an alkyl or alkenyl group (preferably having up to 10 carbon atoms), a cycloalkyl group (preferably having up to 10 carbon atoms), an araliphatic group such as an aralkyl group (preferably having up to 20 carbon atoms), an aryl group (preferably having up to 20 carbon atoms) or a heterocyclic group having up to 20 carbon atoms and one or more heteroatoms selected from O,S and N. Such a hydrocarbyl or heterocyclic grouping may carry one or more functional groups such as halogen atoms or groups of the formulae —$NR^4R^5$, —$CONR^4R^5$, —$OR^6$, —$SR^6$ and —$COOR^7$, where $R^4$ and $R^5$, which may be the same or different are hydrogen atoms, acyl groups or hydrocarbyl groups as defined for $R^1$ and $R^2$; $R^6$ is a hydrogen atom or an acyl group or a group as defined for $R^1$ or $R^2$ and $R^7$ is a hydrogen atom or a group as defined for $R^1$ or $R^2$. Where $R^1$ and $R^2$ represent a divalent grouping this may be an alkylidene, alkenylidene, alkylene or alkenylene group (preferably having up to 10 carbon atoms), which may carry one or more functional groups as defined above.

As indicated above, the diester groupings of formula (I) may be separated by a wide range of groupings. Where it is desired that the polymer should break down into relatively short sections to aid biodegradation, the group $R^3$ which separates the diester units of formula (II) may, for example, be an alkylene or alkenylene group (e.g. containing up to 20, more preferably up to 10 carbon atoms), a cycloalkylene group (preferably having up to 10 carbon atoms), an arylene group (containing one or more aromatic rings and preferably having up to 20 carbon atoms), an aralkylene group (preferably having up to 20 carbon atoms and which may be bonded via the aryl and/or alkyl moieties—such aralkyl groups include, for example, two aryl groups joined by an alkylene chain) or a heterocyclic group having one or more hetero-atoms selected from O, S and N (preferably having up to 20 carbon atoms). The group $R^3$ may carry functional groups, e.g. as set out above for $R^1$ and $R^2$ and/or substituents such as oxo groups; the carbon chains of $R^3$ groups may be interrupted by heteroatoms such as O, N or S, e.g. in conjunction with oxo substituents to form linkages such as ester, thioester or amide groups.

Where the group $R^3$ comprises a polymeric grouping, this may, for example, be a poly(amino acid) such as a polypeptide, or a polyamide, poly(hydroxy acid), polyester, polycarbonate, polysaccharide, polyoxyethylene, polyvinyl alcohol or polyvinyl ether/alcohol grouping.

The wide range of possible groups $R^1$, $R^2$ and $R^3$ enables the hydrophobicity or hydrophilicity of the polymer to be adjusted to any required use. Thus, the polymers may be water-soluble or water-insoluble.

Aliphatic groups present as, for example, $R^1$ and $R^2$ may be straight or branched, saturated or unsaturated and include, for example, alkyl and alkenyl groups, e.g. methyl, ethyl, isopropyl, butyl or allyl groups. Araliphatic groups include (monocarbocyclic aryl)-alkyl groups, for example benzyl groups. Aryl groups include mono- or bi-cyclic aryl groups, for example phenyl, tolyl or naphthyl groups. Heterocyclic groups include 5- or 6-membered heterocyclic groups preferably having one heteroatom, for example furyl, thienyl or pyridyl groups. Halogen atom substituents may, for example, be chlorine, bromine or iodine.

Polymers according to the invention carrying functional groups or double bonds may serve as substrates for subsequent covalent attachment of biologically active materials such as drugs (e.g. antibacterial or antineoplastic agents), steroids and other hormones, and agrochemicals such as weedkillers and pesticides, or of materials such as diagnostic agents (e.g. X-ray and MRI contrast agents) and may be sold in this form to users who will attach their own active material. However, the invention also extends to polymers containing units of formula (III) wherein $R^1$, $R^2$ and/or $R^3$ carry covalently-attached biologically active or diagnostic materials. Suitable active materials are exhaustively listed in U.S. Pat. No. 4,180,646 referred to above, the contents of which are incorporated herein by reference.

In general, any biodegradation of the diester groupings of formula (I) will take place by enzymic hydrolytic cleavage of the bonds linking the group —O—$C(R^1R^2)$—O— to the adjacent carbonyl groups, generally yielding an aldehyde or ketone of the formula $R^1$—CO—$R^2$. The intervening sections, typified by —CO—$(O)_m$—$R^3$—$(O)_n$—CO— in the polymers of formula (III) will form different products according to whether m or n is 0 or 1. Where m or n is 0, hydrolytic cleavage will generally yield a carboxyl group; where m or n is 1, a hypothetical carbonic acid group —$R^3$—O—COOH is formed which generally eliminates carbon dioxide to form a grouping —$R^3$—OH. This can be of use where liberation of carbon dioxide is physiologically or functionally desirable.

Polymers used for medical purposes must form nontoxic, physiologically acceptable degradation products. Thus, the groups $R^1$, $R^2$ and $R^3$ should be such that degradation products such as the compound $R^1$—CO—$R^2$ and the products HOOC—$R^3$—COOH, HO—$R^3$—COOH or HO—$R^3$—OH are physiologically acceptable and readily dispersible, preferably being water-soluble. Carbon dioxide liberated by cleavage of the carbonate groupings will normally be physiologically acceptable.

As indicated above, the units of formula (III) may be different within the same polymer, i.e. the polymers may be copolymers such as block or graft copolymers. The polymers may be copolymers formed with non-biodegradable monomers; the non-biodegradable sections remaining after enzymic or other cleavage are preferably of acceptable size to ensure their water-solubility or water-dispersibility and thus permit ready dispersal or removal: it is possible to consider such non-biodegradable sections as part of the groupings $R^3$ in formula (III) which, in effect, link together the biodegradable groupings of formula (II).

The polymers may be linear, branched or crosslinked. Branched and crosslinked polymers will in general make use of functional groups or double bonds in the corresponding $R^1$, $R^2$ or $R^3$ groups of their monomers. The resulting crosslinked or branched polymers will thus contain some units of formula (III) wherein $R^1$, $R^2$ and/or $R^3$ are substituted with the crosslinking or branched chains. It is particularly useful for the group $R^3$ to be derived from an amino acid which will in general be non-toxic and soluble on cleavage. Dicarboxylic acids such as glutamic or aspartic acid can be used to make polymers containing —CO—$R^3$—CO— units while hydroxy-amino acids such as serine or threonine can be used to make polymers containing —CO—O—$R^3$—CO— units. The α-amino group of the amino acid will comprise a functional amino substituent on $R^3$ or the point of attachment of a branching or crosslinking chain. Crosslinking agents can for example include di- or polyfunctional molecules such as diols (for linking carboxyl groups) or diacids or diisocyanates (for linking hydroxyl or amino groups).

In general, where the carbon atoms linking the groups $R^3$ to the groupings of formula (II) are chiral, the chirality is preferably that found in natural products since the degrading enzymes will generally act more efficiently on such structures. The L-configuration of amino-acid units is thus preferred. However D-isomers are also cleavable and it may be more convenient in many instances to use isomer mixtures rather than material of only the optimal chirality. It is possible to make use of the different rates of enzymic hydrolysis of D- and L-isomers to produce a controlled rate of degradation.

It has been generally observed that in crosslinked biodegradable polymers the crosslinking sections are often degraded first, thus exposing the rest of the network to enzymic hydrolysis. It is particularly useful, therefore, to have groupings of formula (II) in the crosslinking chains of a polymer. One possibility is thus to convert a water-soluble long chain natural or synthetic non-biodegradable or slowly biodegradable substance, e.g. a protein such as gelatin or albumin, a polysaccharide or oligosaccharide, or a short chain polyacrylamide, into a water-insoluble form by crosslinking using crosslinking units containing groupings of formula (II). This may minimise the cost of the final product by reducing the amount of the relatively expensive biodegradable units of formula (II).

Block copolymers may, for example, have the structure

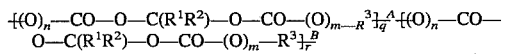

where the respective values of $R^1$, $R^2$, $R^3$ m and n are such that the repeating units in blocks A and B are different and q and r are integers, e.g. 10–20. One or more further blocks may be attached to those shown above.

The polymers of the invention may be prepared in any convenient way, for example by one of the methods set out below.

(A) Synthesis of a homopolymer comprising units of formula (III) in which n is 0 and m is 0 or 1 by condensation polymerisation of a compound of the formula (VI)

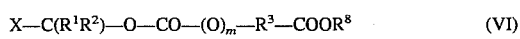

where $R^8$ is a metal ion such as silver, sodium, potassium or lithium, X is a leaving group, e.g. chlorine, bromine, iodine or a hydrocarbylsulphonyloxy group such as a mesyloxy or tosyloxy group, m is 0 or 1 and $R^1$, $R^2$ and $R^3$ have the above meanings.

The compound of formula (VI) may be prepared by reaction of the corresponding acid in which $R^8$ is hydrogen with an appropriate base, whereupon polymerisation will normally take place in situ.

The acid of formula (VI) in which $R^8$ is hydrogen and m is 1 may be prepared by condensation of a compound of formula (VII)

with a compound of formula (VIII)

where $X^1$ is a chlorine bromine or iodine atom and $R^1$, $R^2$, $R^3$ and X have the above meanings. The reaction is preferably effected in the presence of a weakly nucleophilic base such as pyridine in a solvent for the reactants such as a halogenated hydrocarbon, e.g. chloroform.

The acid of formula (VI) in which $R^8$ is hydrogen and m is 0 may be prepared by reaction of a compound of the formula (IX)

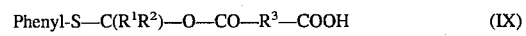

(where $R^1$, $R^2$ and $R^3$ have the above meanings) with a halogenating agent such as sulphonyl chloride, conveniently in a halogenated hydrocarbon solvent such as dichloromethane.

The compound of formula (IX) may be made by reaction of a compound of formula (X)

with a compound of the formula (XI)

where $R^1$, $R^2$, $R^3$ and $X^1$ have the above meanings, conveniently in a polar solvent such as dimethylformamide.

(B) Synthesis of a homopolymer comprising units of formula (III) in which m and n are 0 by condensation of a compound of the formula (XII)

$$R^8O\text{—}CO\text{—}R^3\text{—}CO\text{—}OR^8 \quad \text{(XII)}$$

where $R^8$ is a metal ion as defined above and $R^3$ has the above meaning, with a compound of the formula (XIII)

$$X\text{—}C(R^1R^2)\text{—}X \quad \text{(XIII)}$$

where the groups X, which may be the same or different have the meanings given above, preferably chlorine, bromine or iodine, and $R^1$ and $R^2$ have the above meanings. The compound of formula (XII) may be prepared from the corresponding acid in which $R^8$ is hydrogen by reaction with an appropriate base, whereupon polymerisation will normally take place in situ.

The acid of formula (XII) wherein $R^8$ is hydrogen and m is 0 may be prepared by deprotecting the corresponding compound of formula (XII) in which $R^8$ is a carboxyl protecting group, e.g. a readily hydrolysed group such as t-butyl. This may be removed by addition of base, e.g. sodium or potassium hydroxide to yield compound (XII) directly and hence initiate polymerisation.

(C) Condensation polymerisation of a compound of the formula $HR^9\text{—}R^{3A}\text{—}(O)_n\text{—}CO\text{—}O\text{—}C(R^1R^2)\text{—}O\text{—}CO\text{—}(O)_m\text{—}R^{3B}\text{—}COOH$ where $R^1$, $R^2$, m and n have the above meanings, $R^{3A}$ and $R^{3B}$ are each groups as defined for $R^3$ and $R^9$ is O or $NR^4$ (where $R^4$ is a hydrogen atom, an acyl group or a hydrocarbyl group as defined for $R^1$), to give a polymer with repeating units (XIV)

$$\text{—}[R^9\text{—}R^{3A}\text{—}(O)_n\text{—}CO\text{—}O\text{—}C(R^1R^2)\text{—}O\text{—}CO\text{—}(O)_m\text{—}R^{3B}\text{—}CO]\text{—} \quad \text{(XIV)}$$

Such a polymer may be formed under the conditions conventional for polyester or polyamide condensations. It will be appreciated that such a repeating unit (XIV) corresponds to a unit of formula (III) in which $R^3$ comprises the grouping $\text{—}R^{3B}\text{—}CO\text{—}R^9\text{—}R^{3A}\text{—}$.

The starting material may be formed by deprotection of the corresponding compound having a protected carboxyl and/or $\text{—}R^9H$ group. The latter may be synthesised by reacting a compound of the formula (XV)

$$HO\text{—}C(R^1R^2)\text{—}O\text{—}CO\text{—}(O)_m\text{—}R^{3B}\text{—}COOR^A \quad \text{(XV)}$$

where $R^1$, $R^2$, $R^{3B}$ and m have the above meanings and $R^A$ is a protecting group, with a compound (XVI)

$$R^BR^9\text{—}R^{3A}\text{—}(O)_n\text{—}CO\text{—}Cl \quad \text{(XVI)}$$

where $R^{3A}$, $R^9$ and n have the above meanings and $R^B$ is a protecting group.

The compound (XV) may be prepared by coupling a compound (XVII)

$$R^CO\text{—}C(R^1R^2)\text{—}OH \quad \text{(XVII)}$$

with a compound (XVIII)

$$Cl\text{—}CO\text{—}(O)_m\text{—}R^{3B}\text{—}COOR^A \quad \text{(XVIII)}$$

where $R^1$, $R^2$, $R^{3B}$, $R^A$ and m have the above meanings and $R^C$ is a protecting group which is subsequently removed. The compound of formula (XVII) may be made by reaction of a compound $R^1\text{—}CO\text{—}R^2$ as defined above with an alcohol $R^COH$ to form a hemiacetal.

(D) Reaction of a compound $R^1\text{—}CO\text{—}R^2$, optionally together with a compound $HO\text{—}R^3\text{—}OH$, with phosgene in the presence of a base such as pyridine to give a product containing units of the formula (XIX).

$$\text{—}[CO\text{—}O\text{—}C(R^1R^2)\text{—}O\text{—}CO\text{—}O\text{—}R^3\text{—}O]\text{—} \quad \text{(XIX)}$$

Some units will be formed of the formula (XX)

$$\text{—}[CO\text{—}O\text{—}C(R^1R^2)\text{—}O\text{—}CO\text{—}O\text{—}C(R^1R^2)\text{—}O]\text{—} \quad \text{(XX)}$$

but it should be noted that the definition of $R^3$ given above includes $\text{—}C(R^1R^2)\text{—}$, so that the latter units are within the definition of formula (III). Homopolymers containing such units may also be produced by reaction of the compound $R^1\text{—}CO\text{—}R^2$ with phosgene in the presence of a base such as pyridine.

(E) Reaction of a compound of the formula (XXI)

$$R^{10}\text{—}R^{3A}\text{—}(O)_n\text{—}CO\text{—}O\text{—}C(R^1R^2)\text{—}O\text{—}CO\text{—}(O)_m\text{—}R^{3B}\text{—}R^{11} \quad \text{(XXI)}$$

(where $R^1$, $R^2$, $R^{3A}$, $R^{3B}$, m and n have the above meanings and $R^{10}$ and $R^{11}$, which may be the same or different, optionally together with the groups $R^{3A}$ and $R^{3B}$ to which they are attached, are reactive functional groupings) with a difunctional compound of the formula (XXII)

$$R^{12}\text{—}R^{3C}\text{—}R^{13} \quad \text{(XXII)}$$

where $R^{3C}$ is a group as defined for $R^3$ and $R^{12}$ and $R^{13}$, which may be the same or different, are reactive functional groups capable of reacting with $R^{10}$ and $R^{11}$ whereby a polymer according to the invention is formed, or $R^{12}$ and $R^{13}$ separately or together form a polymerisable group or groups capable of interaction with $R^{10}$ and $R^{11}$, for example so as to generate a polymerised version of compound (XXII) containing crosslinking groups derived from compound (XXI).

The functional groupings $R^{10}$ and $R^{11}$ may, for example, be leaving groups such as halogen atoms e.g. chlorine or bromine (as in haloalkyl groups; α-halomethyl ester groups; α-halomethyl keto groups; or halocarbonyl or halosulphonyl groups such as alkanoyl or sulphonyl halides) or sulphonate ester groups, e.g. alkyl sulphonate esters such as mesyloxy groups and aromatic sulphonate esters such as tosyloxy groups; or activated carboxyl groups, e.g. symmetrical or mixed anhydrides; or activated hydroxyl groups; or with $R^{3A}$ and/or $R^{3B}$ form activated alkenes, e.g. α,β-unsaturated ketones and esters; epoxy groups; or aldehyde and ketone groups and acetals and ketals thereof.

The compound (XXII) may, for example, be a relatively short divalent monomer or preformed polymer whereby a copolymer is formed, or a polyvalent natural or synthetic polymeric material such as a protein or carbohydrate which will be crosslinked by the reagent of formula (XXI). In such cases the groups $R^{12}$ and $R^{13}$ may be nucleophilic groups such as hydroxyl or amino, which commonly occur in natural polymers such as carbohydrates and proteins and which will react with the groupings $R^{10}$ and $R^{11}$ listed above. It will be appreciated that $R^{10}$ and $R^{11}$ may equally be groups such as hydroxyl or amino, while $R^{12}$ and $R^{13}$ are groups reacting with these as listed for $R^{10}$ and $R^{11}$.

Polymerisable compounds of formula (XXII) include those in which $R^{12}$ and $R^{13}$ form an optionally substituted ethylenically unsaturated group, e.g. a vinyl group. Examples of such compounds thus include vinyl monomers such as vinyl acetate and styrene and acrylic and methacrylic monomers such as acrylic acid, methacrylic acid, methyl acrylate, methyl methacrylate, acrylamide, methacrylamide, acrylonitrile, methacrylonitrile, hydroxyethyl methacrylate and hydroxypropyl methacrylate. Compounds of this type may be copolymerised with compounds of formula (XXI) in which $R^{10}$ and $R^{11}$ comprise ethylenically unsaturated groups, e.g. under conditions appropriate for free radical polymerisation, to yield appropriately crosslinked polymers.

Reagents of formula (XXI) are new and constitute a further feature of the invention.

Polymers in accordance with the invention may, for example, be produced in a single solution phase whereby a mass of insoluble polymeric material is formed; after solvent removal this material may be shaped for the required end use e.g. as sheets, fibres, particles or articles such as surgical implants. Un-crosslinked polymers according to the invention will in general be thermoplastic and so may be shaped (e.g. by calendering, drawing or moulding) at elevated temperature to form a particular desired product. Films of polymers according to the invention may, for example, be made by solvent casting.

The polymers may also be produced by emulsion polymerisation to give particles of the polymeric material; a solution of the monomer(s) in a water-immiscible organic solvent may be dispersed in an aqueous phase and polymerisation then initiated. Thus, for example, in reactions (A) and (B) above, where formation of a salt initiates polymerisation, the acid (VI) in reaction (A) or the protected acid (XII) in reaction (B) may be dissolved in an organic solvent such as a halogenated hydrocarbon and emulsified, for example by sonication. Addition of a base such as sodium hydroxide to the aqueous phase, optionally with a phase transfer agent, then initiates polymerisation. Heating may be desirable to promote polymerisation. Methods of emulsion polymerisation to produce particles, especially monodisperse particles, are described in EP-A-0003905, EP-A-0091453, EP-A-0010986 and EP-A-0106873.

Polymers according to the invention, e.g. containing units of formula (III) as hereinbefore defined, find utility in, for example, surgical implants such as sutures, soft tissue prostheses, sponges, films (e.g. artificial skin) or wound dressings (e.g. hydrogel sheets), flexible sheet materials and articles such as containers formed therefrom. Such polymers are advantageously biodegradable. Biodegradable polymers also find use in, for example, the manufacture of biodegradable delayed release formulations for drugs or agricultural chemicals, and horticultural aids such as water-retaining "mulch" sheeting and plant containers. Such usages and the polymers shaped for use therein comprise further features of the invention. For use as prostheses, the shaped polymers may advantageously carry heparin, at least on the surface thereof.

Where a polymer of the invention is to be used as a biodegradable delayed release agent, the active material may be contained within a shell of the biodegradable polymer, e.g. in a capsule or in microspheres, or it may be physically incorporated during polymerisation so that it is uniformly distributed within the polymer and is released during biodegradation. Alternatively, the active material may comprise all or part of any of the groups $R^1$, $R^2$ or $R^3$ and thus be released by the enzymatic cleavage. Typical drugs for incorporation in delayed release formulations include steroids, contraceptives, antibacterials, narcotics-antagonists and anti-tumour drugs.

The polymers of the invention, when of appropriately short chain length, may be used as plasticisers for other polymers. Where the polymers of the invention are biodegradable, degradation of the plasticiser thus either breaks up the integrity of the material or opens it up to attack by enzymes.

Biodegradable polymer particles according to the invention can also advantageously be used for diagnostic purposes. Thus an X-ray contrast agent, which will normally be a poly-iodo aromatic compound, may form all or part of the group $R^3$ or $—C(R^1R^2)—$ so that it is liberated and safely eliminated from the body on biodegradation. Such particles may be used for visualisation of the liver and spleen since they are trapped in the reticuloendothelial systems of those organs. The X-ray contrast agent may also be simply held physically in the polymers by being incorporated during polymerisation.

Polymer particles according to the invention may also contain paramagnetic, superparamagnetic or ferromagnetic substances which are of use in magnetic resonance imaging (MRI) diagnostics. Thus, submicron particles of iron or a magnetic iron oxide can be physically incorporated into the polymers during polymerisation to provide ferromagnetic or superparamagnetic particles. Paramagnetic MRI contrast agents principally comprise paramagnetic metal ions, such as gadolinium ions, held by a chelating agent which prevents their release (and thus substantially eliminates their toxicity). Such chelating agents with complexed metal ions may be physically held in the polymers by being present during polymerisation or the groups $R^1$, $R^2$ and $R^3$ may comprise suitable chelating groups. In general many such chelating agents are poly-amino polycarboxylic acids such as diethylene triamine pentaacetic acid (R. B. Lauffer, Chem. Rev. 87 (1987), pp. 901–927).

Polymer particles of the invention may also contain ultrasound contrast agents such as heavy materials, e.g. barium sulphate or iodinated compounds such as the X-ray contrast agents referred to above, to provide ultrasound contrast media.

The following Examples are given by way of illustration only.

EXAMPLE 1

Poly(1,6-dioxa-2,5-dioxoheptylene)

To a mixture of di-sodium succinate (1.0 equiv.) in an appropriate amount of dimethylformamide is added diiodomethane (1.0 equiv.). The reaction mixture is stirred at ambient temperature until the main amount of the reagents are consumed, dialysed to remove low molecular weight material, and evaporated to give the title double ester polymer having repeating units of formula

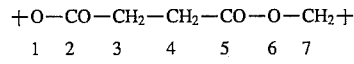

i.e. units (II) in which $R^1=R^2=H$, $R^3=-CH_2-CH_2-$ and $m=n=0$.

EXAMPLE 2

Poly(2,6-dimethyl-4,7-dioxo-1,3,5-trioxaheptylene)

To a mixture of 1-chloroethyl chloroformate (1.1 equiv.) and (S)-2-hydroxypropionic acid (1.0 equiv.) in an appropriate amount of dimethylformamide is added dropwise pyridine (1.0 equiv.) at a temperature below 12° C. The reaction mixture is stirred at ambient temperature until the majority of the reagents are consumed, dialysed to remove low molecular weight material, and evaporated to give the title carbonate ester polymer having repeating units of formula

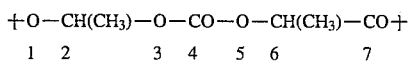

i.e. units (II) in which $R^1$=H, $R^2$=$CH_3$, $R^3$=$CH(CH_3)$, m=1 and n=0.

EXAMPLE 3 a) Mono-glycoyloxymethyl succinate

To a mixture of sodium glycolate (1.0 equiv.) in an appropriate amount of dimethylformamide, is dropwise added benzyl chlorometyl succinate (1.0 equiv.—prepared in accordance with Benneche, Strande and Wiggen, Acta Chem. Scand. 43 (1988), pp. 74–77) in dimethylformamide at ambient temperature. The reaction mixture is stirred at 50° C. until the majority of the reactants are consumed, concentrated, and extracted into chloroform/sodium carbonate solution. The organic phase is dried and evaporated to give the benzyl ester of the title product. Catalytic hydrogenation in conventional manner removes the benzyl group, and the title compound is thus obtained, having the formula

HO—CO—CH$_2$—CH$_2$—CO—O—CH$_2$—O—CO—CH$_2$—OH b) Poly(5,7,10-trioxa-1,4,8-trioxodecylene)

A mixture of mono-glycoyloxymethyl succinate and a catalytic amount of p-toluenesulphonic acid in dry toluene is refluxed under a nitrogen atmosphere until water ceases to form. The solvent is removed at 200° C. and a pressure of 0.1 mm Hg, to give the title polymer having repeating units of the formula

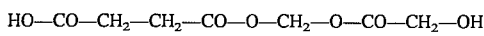

i.e. units (II) in which $R^1$=$R^2$=H, $R^3$=—CH$_2$—O—CO—CH$_2$—CH$_2$— and m=n=0.

EXAMPLE 4 a) Methylene dimethacrylate

A solution of potassium hydroxide (1.00M, 40.00 ml) is added to methacrylic acid (3.44 g, 40.00 mmol) at 0° C. and the solution freeze dried for 16 hours. Dry dimethylformamide (230 ml) is added and the suspension heated to 60° C. under a dry nitrogen atmosphere. Diiodomethane (1.61 ml, 20.00 mmol) is added in two portions during 10 min. and the reaction mixture left for 4 days at 60° C. The solvent is removed under reduced pressure (0.05 mm Hg), before diethyl ether (140 ml), saturated aqueous sodium hydrogen carbonate (50 ml) and water (50 ml) are added. The aqueous layer is extracted with diethyl ether (6×60 ml) and the combined ether extracts washed with water (4×50 ml), dried (MgSO$_4$), and evaporated to give 2.63 g (72%) of the title compound. $^1$H NMR (60 MHz, CDCl$_3$): δ 1.97 (2×CH$_3$, m), 5.63 (2×H—C=, m), 5.88 (CH$_2$, s), 6.18 (2×H—C=, m). IR (film, cm$^{-1}$): 2987 (w), 2962 (w), 2930 (w), 1732 (str), 1638 (w), 1454 (w), 1315 (w), 1295 (w), 1158 (w), 1100 (str), 1012 (m), 989 (m).

b) Methylene diacrylate

A solution of potassium hydroxide (1.00M, 40.00 ml) is added to acrylic acid (2.88 g, 40.00 mmol) at 0° C. and the solution freeze dried for 16 hours. Dry dimethylformamide (200 ml) is added and the suspension heated to 60° C. under a dry nitrogen atmosphere. Diiodomethane (1.61 ml, 20.00 mmol) is added in two portions during 10 min. and the reaction mixture left for 4 days at 60° C. The solvent is removed under reduced pressure (0.05 mm Hg), before diethyl ether (140 ml), saturated aqueous sodium hydrogen carbonate (50 ml) and water (50 ml) are added. The aqueous layer is extracted with diethyl ether (6×60 ml) and the combined ether extracts washed with water (4×50 ml), dried (MgSO$_4$), and evaporated to give 1.06 g (34%) of the title compound. $^1$H NMR (60 MHz, CDCl$_3$): δ 5.81–6.61 (2×CH$_2$=CH—, m), 5.84 (CH$_2$, s).

c) Chloromethyl (2-methacryloyloxy)ethyl carbonate

Pyridine (0.89 ml, 11.00 mmol) is added dropwise to a solution of chloromethyl chloroformate (0.89 ml, 11.00 mmol) and 2-hydroxyethyl methacrylate (1.22 ml, 10.00 mmol) in dichloromethane (12 ml) at 0° C. under a dry nitrogen atmosphere. After 21 hours at 20° C. the reaction mixture is washed with hydrochloric acid (1.00M, 10 ml), saturated aqueous sodium hydrogen carbonate (10 ml) and water (10 ml). The organic phase is dried (MgSO$_4$) and the solvent evaporated under reduced pressure (10 mm Hg) to give 1.97 g (88%) of the title compound. $^1$H NMR (60 MHz, CDCl$_3$): δ 1.88 (CH$_3$, d, J=2 Hz), 4.35 (O—CH$_2$—CH$_2$—O, m), 5.47 (H—C=, m), 5.63 (CH$_2$—Cl, s), 6.00 (H—C=, m).

d) (2-Methacryloyloxy)ethyl methacryloyloxymethyl carbonate

A solution of potassium hydroxide (1.00M, 5.00 ml) is added to methacrylic acid (0.43 g, 5.00 mmol) at 0° C. and the solution freeze dried during 16 hours. Dry dimethylformamide (50 ml) is added and to the resulting suspension is added chloromethyl (2-methacryloyloxy)ethyl carbonate (1.11 g, 5.00 mmol). 18-Crown-6 (0.066 g, 0.25 mmol) is added as a catalyst and the reaction left under a dry nitrogen atmosphere. After 24 hours at 20° C. and 6 days at 4° C. the solvent is removed under reduced pressure (0.05 mm Hg) and diethyl ether (30 ml) and water (20 ml) added. The aqueous layer is extracted with diethyl ether (3×20 ml) and the combined ether extracts washed with water (20 ml), dried (MgSO$_4$) and evaporated to give 1.26 g (93%) of the title compound. $^1$H NMR (60 MHz, CDCl$_3$): δ 1.97 (2×CH$_3$, m), 4.38 (O—CH$_2$—CH$_2$—O, m), 5.53 (2×H—C=, m), 5.77 (CH$_2$, s), 6.07 (2×H—C=, m).

e) Ethylene di(chloromethyl carbonate)

Pyridine (0.89 ml, 11.00 mmol) is added dropwise to a solution of chloromethyl chloroformate (1.32 ml, 14.83 mmol) and ethylene glycol (0.28 ml, 5.00 mmol) in dichloromethane (10 ml) at 7° C. with good stirring under a dry N$_2$ atmosphere. After 15 min. at 7° C. and 6 hours at 20° C. the reaction mixture is transferred to a separating funnel with the aid of dichloromethane (10 ml). The reaction mixture is washed with hydrochloric acid (1.00M, 10 ml), saturated aqueous sodium hydrogen carbonate (10 ml) and water (10 ml). The organic phase is dried (MgSO$_4$) and the solvent evaporated under reduced pressure to give 1.12 g (90%) of the title product. $^1$H NMR (300 MHz, CDCl$_3$): δ 4.48 (s, O—CH$_2$CH$_2$—O), 5.75 (s, 2×Cl—CH$_2$—O). $^{13}$C NMR (75 MHz, CDCl$_3$): δ 65.8 (O—CH$_2$CH$_2$—O), 72.2 (2×Cl—CH$_2$—O), 153.0 (2×C=O).

f) Bis(2-chloromethoxycarbonyloxyethyl)ether

Pyridine (0.89 ml, 11.00 mmol) is added dropwise to a solution of chloromethyl chloroformate (1.32 ml, 14.83 mmol) and diethylene glycol (0.47 ml, 5.00 mmol) in dichloromethane (10 ml) at 7° C. with good stirring under a dry N$_2$ atmosphere. After 10 min. at 7° C. and 6 hours at 20° C. the reaction mixture is transferred to a separating funnel with the aid of dichloromethane (10 ml). The reaction mixture is washed with hydrochloric acid (1.00M, 10 ml), saturated aqueous sodium hydrogen carbonate (10 ml) and water (10 ml). The organic phase is dried (MgSO$_4$) and the solvent evaporated under reduced pressure (10 mm Hg) to give 1.26 g (86%) title product. $^1$H NMR (300 MHz, CDCl$_3$): δ 3.72 (m, 2×CH$_2$—O), 4.34 (m, 2×CH$_2$—O—C=O), 5.71 (s, 2×Cl—CH$_2$—O). $^{13}$C NMR (75 MHz, CDCl$_3$): δ 67.6 (2×CH$_2$—O), 68.5 (2×CH$_2$—O—C=O), 72.1 (2×Cl—CH$_2$—O), 153.2 (2×C=O).

g) 1-Chloroethyl 2-methacryloyloxyethyl carbonate

Pyridine (0.89 ml, 11.00 mmol) is added dropwise to a solution of 1-chloroethyl chloroformate (1.20 ml, 11.00 mmol) and 2-hydroxyethyl methacrylate (1.22 ml, 10.00 mmol) in dichloromethane (12 ml) at 3° C. under a dry N$_2$ atmosphere. After 15 min. at 3° C. and 17 hours at 20° C. the reaction mixture is transferred to a separating funnel with the aid of dichloromethane (10 ml). The reaction mixture is washed with hydrochloric acid (1.00M, 10 ml), saturated aqueous sodium hydrogen carbonate (10 ml) and water (2×10 ml). The organic phase is dried (MgSO$_4$) and the solvent evaporated under reduced pressure to give 1.76 g (74%) of the title product. $^1$H NMR (60 MHz, CDCl$_3$): δ 1.85 (3 H, d, J=6 Hz, CH$_3$—CH), 1.96 (3 H,d, J=2 Hz, CH$_3$—C=), 5.55 (1 H, m, CH=), 6.10 (1 H, m, CH=), 6.38 (1 H, k, J=6 Hz, CH—CH$_3$).

h) Chloromethyl 4-acryloyloxybutyl carbonate

Pyridine (0.89 ml, 11.00 mmol) is added dropwise to a solution of chloromethyl chloroformate (0.98 ml, 11.00 mmol) and 4-hydroxybutyl acrylate (1.38 ml, 10.00 mmol) in dichloromethane (12 ml) at 3° C. under a dry N$_2$ atmosphere. After 15 min. at 3° C. and 17 hours at 20° C. the reaction mixture is transferred to a separating funnel with the aid of dichloromethane (10 ml). The reaction mixture is washed with hydrochloric acid (1.00M, 10 ml), saturated aqueous sodium hydrogen carbonate (10 ml) and water (2×10 ml). The organic phase is dried (MgSO$_4$) and the solvent evaporated under reduced pressure to give 1.76 g (74%) of the title product. $^1$H NMR (60 MHz, CDCl$_3$): δ 1.82 (4 H, m, CH$_2$—CH$_2$), 4.27 (4 H, m, 2×CH$_2$—O), 5.77 (2 H, s, Cl—CH$_2$—O), 5.8–6.7 (3 H, m, CH=CH$_2$).

i) 1-Chloroethyl 4-acryloyloxybutyl carbonate

Pyridine (0.89 ml, 11.00 mmol) is added dropwise to a solution of 1-chloroethyl chloroformate (1.20 ml, 11.00 mmol) and 4-hydroxybutyl acrylate (1.38 ml, 10.00 mmol) in dichloromethane (12 ml) at 3° C. under a dry N$_2$ atmosphere. After 15 min. at 3° C. and 17 hours at 20° C. the reaction mixture is transferred to a separating funnel with the aid of dichloromethane (10 ml). The reaction mixture is washed with hydrochloric acid (1.00M, 10 ml), saturated aqueous sodium hydrogen carbonate (10 ml) and water (2×10 ml). The organic phase is dried (MgSO$_4$) and the solvent evaporated under reduced pressure to give 2.26 g (90%) of the title product. $^1$H NMR (60 MHz, CDCl$_3$): δ 1.80 (4 H, m, CH$_2$—CH$_2$), 1.86 (3 H, d, J=5 Hz, CH$_3$), 4.24 (4 H, m, 2×CH$_2$—O), 5.7–6.6 (4 H, m, CH=CH$_2$ and CH).

j) 1-Methacryloyloxyethyl 2-methacryloyloxyethyl carbonate

1-Chloroethyl 2-methacryloyloxyethyl carbonate (1.183 g, 5.00 mmol) is added to a suspension of freeze dried potassium methacrylate (0.683 g, 5.50 mmol) and 18-crown-6 (0.066 g, 0.25 mmol) in dimethylformamide (50 ml) under a dry N$_2$ atmosphere. After 5 days at 20° C. the solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried (MgSO$_4$) and the solvent removed under reduced pressure to give 1.10 g (77%) of the title product. $^1$H NMR (60 MHz, CDCl$_3$): δ 1.63 (3 H, d, J=5 Hz, CH$_3$—CH), 1.98 (6 H, s, 2×CH$_3$), 4.42 (4 H, s, O—CH$_2$—CH$_2$—O), 5.62 (2 H, m, CH=), 6.15 (2 H, m, CH=), 6.84 (1 H, k, J=5 Hz, CH—CH$_3$).

k) Acryloyloxymethyl 4-acryloyloxybutyl carbonate

Chloromethyl 4-acryloyloxybutyl carbonate (1.183 g, 5.00 mmol) is added to a suspension of freeze dried potassium acrylate (0.606 g, 5.50mmol) and 18-crown-6 (0.066 g, 0.25 mmol) in dimethylformamide (50 ml) under a dry N$_2$ atmosphere. After 5 days at 20° C. the solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried (MgSO$_4$) and the solvent removed under reduced pressure to give 1.24 g (91%) of the title product. $^1$H NMR (60 MHz, CDCl$_3$): δ 1.82 (4 H, m, CH$_2$—CH$_2$), 4.23 (4 H, m, 2×CH$_2$—O), 5.88 (2 H, s, O—CH$_2$—O), 5.7–6.8 (6 H, 2×CH=CH$_2$).

l) 1-Acryloyloxyethyl 4-acryloyloxybutyl carbonate

1-Chloroethyl 4-acryloyloxybutyl carbonate (1.253 g, 5.00 mmol) is added to a suspension of freeze dried potassium acrylate (0.606 g, 5.50 mmol) and 18-crown-6 (0.066 g, 0.25 mmol) in dimethylformamide (50 ml) under a dry N$_2$ atmosphere. After 5 days at 20° C. the solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried (MgSO$_4$) and the solvent removed under reduced pressure to give 1.28 g (89%) of the title product. $^1$H NMR (60 MHz, CDCl$_3$): δ 1.58 (3 H, d, J=5 Hz, CH$_3$—CH), 1.80 (4 H, m, CH$_2$—CH$_2$), 4.24 (4 H, m, 2×CH$_2$—O), 5.7–6.7 (6 H, m, 2×CH=CH$_2$), 6.87 (1 H, k, J=5 Hz, CH—CH$_3$).

m) Methylene di(p-vinylbenzoate)

Diiodomethane (0.20 ml, 2.50 mmol) is added to a solution of freeze dried potassium p-vinylbenzoate (0.931 g, 5.00 mmol), 18-crown-6 (0.040 g, 0.25 mmol) and hydroquinone (0.011 g, 0.10 mmol) in dimethylformamide (35 ml) under a dry N$_2$ atmosphere and the reaction mixture left for 2.5 days at 60° C. The solvent is removed under reduced pressure and the residue dissolved by adding diethyl ether (20 ml), saturated aqueous sodium hydrogen carbonate (5 ml) and water (10 ml). After separating the phases the aqueous layer is extracted with diethyl ether (6×10 ml) and the combined organic phase washed with water (5×10 ml). The organic phase is dried (MgSO$_4$) and the solvent removed under reduced pressure to give 0.64 g (83%) of the title product. $^1$H NMR (300 MHz, CDCl$_3$): δ 5.39 (2 H, d, J=10 Hz, 2×CH=), 5.86 (2 H, d, J=17.6 Hz, 2×CH=), 6.24 (2 H, s, O—CH2—O), 6.73 (2 H, dd, J=11.0, 17.6, 2×CH=), 7.45 (4 H, 2×d, J=6.8 Hz, Ar), 8.04 (2 H, d, J=6.6 Hz, Ar), 8.05 (2 H, d, J=6.6 Hz, Ar). $^{13}$C NMR (75 MHz, CDCl$_3$): δ 79.8 (O—CH$_2$—O), 116.8 (2×CH=), 126.0, 130.2 (C$_2$,C$_2$',C$_3$, C$_3$'), 127.8, 142.5 (C$_1$,C$_1$',C$_4$,C$_4$'), 135.7 (2×CH=), 164.9 (2×C=O).

n) Methylene di(p-bromobenzoate)

Diiodomethane (0.60 ml, 7.50 mmol) is added to a solution of freeze dried potassium p-bromobenzoate (3.587 g, 15.00 mmol) and 18-crown-6 (0.198 g, 0.75 mmol) in dimethylformamide (100 ml) under a dry N$_2$ atmosphere and the reaction mixture left for 4 days at 60° C. The solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried ($MgSO_4$) and the solvent removed under reduced pressure to give 2.62 g (84%) of the title product. $^1$H NMR (60 MHz, $CDCl_3$): δ 6.29 (2 H, s, O—$CH_2$—O), 7.63 (4 H, d, J=9 Hz, Ar), 8.00 (4 H, d, J=9 Hz, Ar).

o) Methylene di(p-hydroxybenzoate)

Diiodomethane (0.40 ml, 5.00 mmol) is added to a solution of freeze dried potassium p-hydroxybenzoate (1.762 g, 10.00 mmol) in dimethylformamide (60 ml) under a dry $N_2$ atmosphere and the reaction mixture left for 4 days at 60° C. The solvent is removed under reduced pressure and the residue dissolved by adding dichloromethane (60 ml) and water (30 ml). After separating the phases the aqueous layer is extracted with dichloromethane (3×30 ml) and the combined organic phase washed with brine (50 ml). The organic phase is dried ($MgSO_4$) and the solvent removed under reduced pressure to give 0.94 g (65%) of the title product. $^1$H NMR (60 MHz, $CDCl_3/CD_3OD$ 1:2): δ 4.92 (2 H, s, 2×OH), 6.18 (2 H, s, O—$CH_2$—O), 6.88 (4 H, d, J=9 Hz, Ar), 7.96 (4 H, d, J=9 Hz, Ar).

p) Methylene bis[p-(hydroxymethylethynyl)benzoate]

Bis (triphenylphosphine)palladium dichloride (17.0 mg, 0.02 mmol) and cuprous iodide (2.0 mg, 0.01 mmol) are added to a suspension of methylene bis (p-bromobenzoate) prepared as described in Example 4 (n) (0.500 g, 1.21 mmol) and propargyl alcohol (0.16 ml, 2.66 mmol) in triethylamine (10 ml) with good stirring, at 20° C., under a dry $N_2$ atmosphere. After 10 days at 20° C., the triethylamine is removed under reduced pressure, water (20 ml) is added and the mixture is extracted with dichloromethane (3×15 ml). The dichloromethane phases are washed with hydrochloric acid (0.5M, 10 ml), dried ($MgSO_4$) and the dichloromethane removed under reduced pressure to give 0.37 g (85%) of the crude product. $^1$H NMR (60 MHz, $CDCl_3$): δ 3.67 (2 H, s, OH), 4.47 (4 H, s, $CH_2$—O), 6.18 (2 H, s, O—$CH_2$—O), 7.2–7.5 (4 H, Ar), 7.8–8.0 (4 H, Ar).

q) Adipic acid bis 1-chloroethyl ester

Anhydrous zinc chloride (10.0 mg, 0.07 mmol) is added to adipoyl chloride (2.92 ml, 20.00 mmol) at 20° C., under a dry $N_2$ atmosphere. Acetaldehyde (2.26 g, 40.00 mmol) is added dropwise to the reaction mixture at −5° C. The reaction temperature is kept between −5° C. and 0° C. and dichloromethane (20 ml) is added. The zinc chloride catalyst is removed by passing the reaction mixture through a chromatography column containing aluminium oxide (Fluka 06290, type 5016 A basic, 20 g) at 5° C. using dichloromethane as the solvent. The solvent is removed under reduced pressure to give 3.64 g (67%) of the crude product. $^1$H NMR (60 MHz, $CDCl_3$): δ 1.5–1.9 (4 H, m, $CH_2$—$CH_2$), 1.77 (6 H, d, J=6 Hz, 2×$CH_3$), 2.1–2.5 (4 H, m, 2×$CH_2$—O), 6.49 (2 H, k, J=6 Hz, 2×Cl—CH—O).

EXAMPLE 5 a) Acrylamide polymer powder crosslinked with 5% methylene dimethacrylate

Methylene dimethacrylate prepared as described in Example 4(a) (0.50 g, 2.72 mmol) dissolved in dimethylformamide (2 ml) is added to a solution of acrylamide (10.00 g, 140.70 mmol) and azobisisobutyronitrile (AIBN, 0.02 g, 0.86 mmol) in dimethylformamide and the reaction mixture heated to 60° C. under a dry nitrogen atmosphere. After approximately 50 min. the clear reaction mixture turns into a white suspension. The reaction mixture is kept at 60° C. for a total of 2 hours to complete the reaction. After cooling to 20° C. the reaction mixture is filtered, the solid washed several times with dimethylformamide and dried under vacuum to yield the title compound as a powder. The product is insoluble in water in contrast to uncrosslinked polyacrylamide prepared by the same method. IR (KBr, cm$^{-1}$): 3379 (broad, str), 3199 (str), 2932 (w), 1739 (m), 1662 (str), 1616 (str), 1451 (m), 1415 (m), 1348 (w), 1320 (w), 1102 (w), 976 (w), 610 (broad, m). On subtracting the spectrum of polyacrylamide prepared using the same procedure as above from the crosslinked polyacrylamide, the following peaks originating from the incorporated crosslinker appear: 1740 (str), 1471 (w), 1387 (w), 1152 (m), 1084 (str), 963 (str).

b) Acrylamide polymer gel crosslinked with 5% methylene dimethacrylate

AIBN (0.01 g, 0.43 mmol) is added to a solution of acrylamide (5.00 g, 70.34 mmol) and methylene dimethacrylate prepared as described in Example 4(a) (0.250 g, 1.36 mmol) in water/DMSO (90:10,20 ml) at 60° C. under a dry nitrogen atmosphere, with good stirring. After approximately 25 min. the reaction mixture turns into a gel and is kept at 60° C. for a total of 2 hours to complete the reaction. The resulting gel is not soluble in water whereas the corresponding acrylamide homopolymer is soluble.

c) Acrylamide polymer crosslinked with 2.6% methylene dimethacrylate

AIBN (0.01 g, 0.43 mmol) is added to a solution of acrylamide (5.00 g, 70.34 mmol) and methylene dimethacrylate prepared as described in Example 4(a) (0.131 g, 0.709 mmol) in water/DMSO (90:10,20 ml) at 60° C. under a dry nitrogen atmosphere, with good stirring. After approximately 25 min. the reaction mixture turns into a gel and is kept at 60° C. for a total of 2 hours to complete the reaction. The resulting gel is not soluble in water whereas the corresponding acrylamide homopolymer is soluble.

d) Acrylamide polymer crosslinked with 1.3% methylene dimethacrylate

AIBN (0.01 g, 0.43 mmol) is added to a solution of acrylamide (5.00 g, 70.34 mmol) and methylene dimethacrylate prepared as described in Example 4(a) (0.065 g, 0.035 mmol) in water/DMSO (90:10, 20 ml) at 60° C. under a dry nitrogen atmosphere, with good stirring. After approximately 25 min. the reaction mixture turns into a gel and is kept at 60° C. for a total of 2 hours to complete the reaction. The resulting gel is not soluble in water whereas the corresponding acrylamide homopolymer is soluble.

The degree of swelling in water of acrylamide-methylene dimethacrylate copolymer gels prepared according to this Example is inversely proportional to the degree of crosslinking as determined by the percentage of methylene dimethacrylate employed.

EXAMPLE 6

Methyl acrylate polymer crosslinked with 2% methylene diacrylate

AIBN (0.005 g, 0.03 mmol) is added to a solution of methyl acrylate (3.029 g, 35.20 mmol) and methylene diacrylate prepared as described in Example 4(b) (0.110 g, 0.70 mmol) in dimethylformamide (10 ml) at 60° C. under a dry $N_2$ atmosphere. After approximately 50 min. the clear reaction mixture turns into a gel. The reaction mixture is kept at 60° C. for a total of 2 hours to complete the reaction. The resulting gel is insoluble in tetrahydrofuran, whereas poly methyl acrylate is soluble. This proves that the gel is crosslinked.

EXAMPLE 7

Acrylic acid polymer crosslinked with 2% methylene diacrylate

AIBN (0.005 g, 0.03 mmol) is added to a solution of acrylic acid (2.534 g, 35.20 mmol) and methylene diacrylate prepared as described in Example 4(b) (0.110 g, 0.70 mmol) in dimethylformamide (10 ml) at 60° C. under a dry $N_2$ atmosphere. After approximately 60 min. the clear reaction mixture turns into a gel. The reaction mixture is kept at 60° C. for a total of 2 hours to complete the reaction. The resulting gel is insoluble in dimethylformamide, whereas poly acrylic acid is soluble. This proves that the gel is crosslinked.

EXAMPLE 8

Acrylamide polymer crosslinked with 0.5% methylene diacrylate

AIBN (0.005 g, 0.03 mmol) dissolved in tetrahydrofuran (2 ml) is added to a solution of acrylamide (2.500 g, 35.17 mmol) and methylene diacrylate prepared as described in Example 4(b) (0.027 g, 0.18 mmol) in tetrahydrofuran (10 ml) at 60° C. under a dry $N_2$ atmosphere. After approximately 2 hours no visible change is observable in the reaction mixture. AIBN (0.005 g, 0.03 mmol) is therefore added. The polymer then starts to precipitate from the reaction mixture and after a total of 5 hours the reaction mixture is cooled and filtered. The polymer is washed several times with tetrahydrofuran and dried under reduced pressure. The resulting polymer is insoluble in water, whereas polyacrylamide is soluble. This proves that a crosslinked polymer is formed. The IR-spectrum of the polymer confirms this structure. Subtracting the IR-spectrum of polyacrylamide prepared by the same procedure as above confirms the incorporation of the crosslinker. The concentration of the crosslinker (0.5%) is, however, too low to give an accurate "subtraction spectrum".

EXAMPLE 9

Acrylamide polymer crosslinked with 0.5% 2-methacryloyloxyethyl methacryloyloxymethyl carbonate AIBN (0.005 g, 0.03 mmol) is added to a solution of acrylamide (2.500 g, 35.20 mmol) and 2-methacryloyloxyethyl methacryloyloxymethyl carbonate prepared as described in Example 4(d) (0.048 g, 0.18 mmol) in tetrahydrofuran (10 ml) at 60° C. under a dry $N_2$ atmosphere. After 2 hours no visible change is observed in the reaction mixture. AIBN (0.005 g, 0.03 mmol) dissovled in tetrahydrofuran (2 ml) is therefore added. The polymer then starts to precipitate from the reaction mixture and after a total of 4 hours the reaction mixture is cooled and filtered. The polymer is washed several times with tetrahydrofuran and dried under reduced pressure. IR (KBr, cm$^{-1}$): 3350 (broad, m), 3198 (m), 2933 (w), 1659 (str.), 1617 (m), 1450 (w), 1420 (w). The polymer is soluble in water giving a viscous solution, suggesting little crosslinking.

EXAMPLE 10

2-Hydroxyethyl methacrylate polymer crosslinked with 0.5% 2-methacryloyloxyethyl methacryloyloxymethyl carbonate AIBN (0.005 g, 0.03 mmol) is added to a solution of 2-hydroxyethyl methacrylate (4.578 g, 35.20 mmol) and 2-methacryloyloxyethyl methacryloyloxymethyl carbonate prepared as described in Example 4(d) (0.0479 g, 0.18 mmol) in tetrahydrofuran (10 ml) at 60° C. under a dry $N_2$ atmosphere. After one hour tetrahydrofuran (10 ml) is added and the reaction mixture turns into a gel. The reaction mixture is kept at 60° C. for a total of 2 hours to complete the reaction. The resulting gel is insoluble in dichloromethane, whereas poly 2-hydroxyethyl methacrylate is soluble. This proves that the gel is crosslinked.

EXAMPLE 11

Methyl methacrylate polymer crosslinked with 2% acryloyloxymethyl 4-acryloyloxybutyl carbonate AIBN (0.005 g, 0.03 mmol) is added to a solution of methyl acrylate (3.029 g, 35.20 mmol) and acryloyloxymethyl 4-acryloyloxybutyl carbonate prepared as described in Example 4(k) (0.192 g, 0.70 mmol) in dimethylformamide (10 ml) at 60° C. under a dry $N_2$ atmosphere. After 1 hour the clear reaction mixture turns into a gel. The reaction mixture is kept at 60° C. for a total of 2 hours to complete the reaction. The resulting gel is insoluble in tetrahydrofuran, whereas poly methyl methacrylate is soluble. This proves that the gel is crosslinked.

EXAMPLE 12

Acrylamide polymer crosslinked with 2% acryloyloxymethyl 4-acryloyloxybutyl carbonate AIBN (0.005 g, 0.03 mmol) is added to a solution of acrylamide (2.502 g. 35.20 mmol) and acryloyloxymethyl 4-acryloyloxybutyl carbonate prepared as described in Example 4(k) (0.202 g, 0.74 mmol) in dimethylformamide (10 ml) at 60° C. under a dry $N_2$ atmosphere. After approximately 40 min. the reaction mixture turns white and the polymer starts to precipitate. The reaction mixture is cooled and filtered after a total of 2 hours at 60° C. The polymer is washed several times with dimethylformamide and dried under reduced pressure. IR (KBr, cm$^{-1}$): 3387 (broad, m), 3195 (m), 2932 (w), 2360 (w), 1661 (str.), 1611 (m), 1451 (w), 1415 (w). The polymer product is insoluble in water, whereas polyacrylamide is soluble. This proves that the polymer is crosslinked.

EXAMPLE 13

Acrylamide polymer crosslinked with 2% 1-acryloyloxyethyl 4-acryloyloxybutyl carbonate AIBN (0.005 g, 0.03 mmol) is added to a solution of acrylamide (2.502 g. 35.20 mmol) and 1-acryloyloxyethyl 4-acryloyloxybutyl carbonate prepared as described in Example 4(l) (0.202 g, 0.70 mmol) in dimethylformamide (10 ml) at 60° C. under a dry $N_2$ atmosphere. After approximately 30 min. the polymer starts to precipitate from the reaction mixture. The reaction mixture is cooled and filtered after a total of 2 hours at 60° C. The polymer is washed several times with dimethylformamide and dried under reduced pressure. IR (KBr, cm$^{-1}$): 3390 (broad, m), 3197 (m), 2933 (w), 1661 (str.), 1611 (m), 1452 (w), 1415 (w). The polymer product is insoluble in water, whereas polyacrylamide is soluble. This provides that the polymer is crosslinked.

EXAMPLE 14

Poly (methylene terephthalate)

A solution of potassium hydroxide (1.00M, 10.00 ml) is added to terephthalic acid (0.83 g, 5.00 mmol) at 0° C. and the solution freeze dried during 16 hours. Dry dimethylformamide (50 ml) is added and the suspension heated to 70° C. under a dry nitrogen atmosphere. Diiodomethane (1.61 ml, 20.00 mmol) and 18-crown-6 (0.066 g, 0.25 mmol) are added and the reaction mixture kept for 3 days at 70° C. and 3 days at 100° C. The solvent is removed under reduced pressure (0.05 mm Hg), whereafter diethyl ether (30 ml) and water (30 ml) are added. The pH of the aqueous suspension is adjusted to 9 with sodium hydroxide (1.00M) before washing with diethyl ether (3×30 ml). The aqueous suspension is centrifuged, the liquid decanted off and the solid resuspended in absolute ethyl alcohol. Centrifugation and decantation are repeated and the solid dried under vacuum to give 0.29 g (32%) of the product as a powder. IR (KBr, cm$^{-1}$): 3400 (w, broad), 1732 (str), 1600 (w), 1558 (w), 1456 (w), 1400 (w), 1288 (m), 1256 (m), 1244 (m), 1158 (w), 1118 (w), 1053 (str), 1014 (m), 978 (m), 727 (m). The solubility properties of the product indicate that a polymer is formed.

EXAMPLE 15

Polymer from ethylene di(chloromethyl carbonate) and terephthalic acid

Ethylene di(chloromethyl carbonate) prepared as described in Example 4(e) (0.489 g, 1.98 mmol) is added to a suspension of freeze dried di-potassium terephthalate (0.480 g, 1.98 mmol) and 18-crown-6 (0.027 g, 0.10 mmol) in dimethylformamide (20 ml). After 2 days at 20° C. the reaction mixture is heated to 60° C. and kept there for 3 weeks. The solvent is removed under reduced pressure and the residue dissolved by adding dichloromethane (60 ml) and water (30 ml). After separating the phases the dichloromethane phase is washed with saturated aqueous sodium hydrogen carbonate (30 ml) and brine (30 ml). The organic phase is dried (MgSO$_4$) and the solvent removed under reduced pressure to give 0.35 g (53%) of the title product. $^1$H NMR (60 MHz, CDCl$_3$): δ 4.47 (4 H, s, O—CH$_2$CH$_2$—O), 6.02 (4 H, s, 2×O—CH$_2$—O), 8.12(4 H, s, Ar). High temperature gel filtration chromatography (GPC) indicates that fractions of the material have a molecular weight exceeding 20,000 with respect to poly(ethylene glycol) as standard.

EXAMPLE 16

Polyester from methylene di(p-hydroxybenzoate) and adipoyl chloride

Pyridine (0.560 ml, 6.94 mmol) is added dropwise to a solution of methylene di(p-hydroxybenzoate) prepared as described in Example 4(o) (1.00 g, 3.47 mmol) and adipoyl chloride (0.635 g, 3.47 mmol) in dry dichloromethane (30 ml) at 20° C. under a dry N$_2$ atmosphere. After 18 hours at 20° C. water (10 ml) is added to the reaction mixture and the phases are separated. The aqueous layer is extracted with dichloromethane (3×10 ml) and the combined organic phases are washed with water (3×20 ml). The volume of the organic phase is increased to 250 ml by adding more dichloromethane. The resulting organic phase is dried (MgSO$_4$) and the solvent evaporated under reduced pressure (0.1 mmHg) to give 0.93 g (67%) product. $^1$H NMR (300 MHz, CDCl$_3$): δ 1.76 (4 H, m, CH$_2$—CH$_2$), 2.59 (4 H, m, 2×CH$_2$—C=O), 6.20 (2 H, s, O—CH$_2$—O), 7.16 (4 H, At), 8.06 (4 H, Ar). High temperature gel filtration chromatography (GPC) indicates that fractions of the material have a molecular weight exceeding 20,000 with respect to poly(ethylene glycol) as standard.

EXAMPLE 17

Polymer from bis (2-chloromethoxycarbonyloxyethyl) ether and di-potassium fumarate Bis(2-chloromethoxycarbonyloxyethyl) ether prepared as described in Example 4(f) (1.456 g, 5.00 mmol) is added to a suspension of di-potassium fumarate (0.961 g, 5.00 mmol) and 18-crown-6 (0.039 g, 0.15 mmol) in DMF (50 ml) and the reaction mixture is heated to 60° C., under a dry N$_2$ atmosphere. After 11 days at 60° C. the solvent is removed under reduced pressure. Chloroform (40 ml) is added to the residue and the organic layer washed with water (3×30 ml). The combined water washings are extracted with chloroform (3×20 ml). The combined organic phases are concentrated in vacuo to give 1.57 g (94%) of a brown oil product. $^1$H NMR (300 MHz, DMSO-d$_6$, 40° C.): δ 3.78 (4 H, m, 2×CH$_2$—O), 4.38 (4 H, m, 2×CH$_2$—O—C=O), 5.94 (4 H, s, 2 ×O—CH$_2$—O), 6.98 (2 H, s, CH=CH). High temperature gel filtration chromatography (GPC) indicates that fractions of the material have a molecular weight exceeding 20,000 with respect to poly(ethylene glycol) as standard.

EXAMPLE 18

Methylene bis [p-2,3-epoxy-1-propyloxy)benzoate]

Potassium tert.butoxide (1.347 g, 12.00 mmol) is added to a solution of methylene di(p-hydroxybenzoate) prepared as described in Example 4(o) (1.728 g, 6.00 mmol) in DMF (75 ml), under a dry N$_2$ atmosphere. Epichlorohydrin (2.22 g, 24.00 mmol) is added and after 24 hours at 20° C. the solvent is removed under reduced pressure. The residue is dissolved by adding dichloromethane (75 ml) and water (30 ml) and adjusting the pH to neutral using hydrochloric acid (1M). After separating the phases the dichloromethane layer is washed with water (3×30 ml). The organic phase is dried (MgSO$_4$) and the solvent removed under reduced pressure to give 1.22 g (51%) product as a colourless oil. $^1$H NMR (60 MHz, CDCl$_3$): δ 2.8 (4 H, m, 2 ×epoxy-CH$_2$), 3.3 (2 H, m, 2×epoxy-CH), 4.05 (2 H, dd, J=22, 11 Hz, 2×O—CH—H), 4.12 (2 H, dd, J=22, 11 Hz, 2×O—CH—H), 6.14 (2 H, s, O—CH$_2$—O), 6.9 (4 H, m, 2×Ar), 7.9 (4 H, m, 2×Ar).

EXAMPLE 19

Hexamethylene di(chloromethyl carbonate)

Pyridine (1.77 ml, 22.00 mmol) is added dropwise to a solution of chloromethyl chloroformate (2.61 ml, 29.70 mmol) and 1,6-hexanediol (1.182 g, 10.00 mmol) in dichloromethane (40 ml) at 7° C. with good stirring under a dry N$_2$ atmosphere. After 15 min. at 7° C. and 6 hours at 20° C. the reaction mixture is transferred to a separating funnel with the aid of dichloromethane (2×10 ml). The reaction mixture is washed with hydrochloric acid (1.00M, 20 ml), saturated aqueous sodium hydrogen carbonate (20 ml) and water (20 ml). Ethyl acetate is added to the organic phase to get a clear solution. This solution is dried (MgSO$_4$) and the solvent evaporated under reduced pressure to give 2.76 g (99%) product. $^1$H NMR (300 MHz, CDCl$_3$): δ 1.2–2.0 [8 H, m, (CH$_2$)$_4$], 4.22 [4 H, t, J=6 Hz, 2×(CH$_2$—O)], 5.73 [4 H, s, 2×Cl—CH$_2$—O)].

EXAMPLE 20

Polymer from adipic acid bis 1-chloroethyl ester and di-potassium terephthalate

Potassium tert.butoxide (1.122 g, 10.00 mmol) is added to a solution of terephthalic acid (0.831 g, 5.00 mmol) in DMF (50 ml) at 20° C., under a dry N$_2$ atmosphere. Adipic acid bis 1-chloroethyl ester prepared as described in Example 4(q) (1.356 g, 5.00 mmol) is added to the resulting suspension and the reaction mixture heated to 60° C. After 1 hour at 60° C., 18-crown-6 (0.066 g, 0.25 mmol) is added. The solvent is removed under reduced pressure after 8 days at 60° C. and the residue dissolved by adding chloroform (60 ml), ethyl acetate (30 ml) and aqueous sodium hydroxide (1M, 50 ml). After separating the phases the aqueous phase is extracted with chloroform (3×25 ml). The combined organic layers are washed with water (2×50 ml) and dried

EXAMPLE 21

Polymer from adipic acid bis 1-chloroethyl ester and di-potassium fumarate

Potassium tert.butoxide (1.122 g, 10.00 mmol) is added to a solution of fumaric acid (0.580 g, 5.00 mmol) in DMF (50 ml) at 20° C., under a dry $N_2$ atmosphere. Adipic acid bis 1-chloroethyl ester prepared as described in Example 4(q) (1.356 g, 5.00 mmol) is added to the resulting suspension and the reaction mixture heated to 60° C. After 1 hour at 60° C., 18-crown-6 (0.066 g, 0.25 mmol) is added. The solvent is removed under reduced pressure after 8 days at 60° C. and the residue dissolved by adding chloroform (60 ml), ethyl acetate (30 ml) and aqueous sodium hydroxide (1 M, 50 ml). After separating the phases the aqueous phase is extracted with chloroform (3×25 ml). The combined organic layers are washed with water (2×50 ml) and dried ($MgSO_4$). The solvent is removed under reduced pressure to give 0.276 g (18%) of crude product.

EXAMPLE 22

Poly(methylene adipoate)

Potassium tert.butoxide (1.122 g, 10.00 mmol) is added to a solution of adipic acid (0.731 g, 5.00 mmol) in DMF (50 ml) at 20° C., under a dry $N_2$ atmosphere. Adipic acid bis chloromethyl ester (prepared according to Rosnati: Bovet. Rend. 1st. super Sanita 15 (1951), 473, 486) (1.215 g, 5.00 mmol) is added to the resulting suspension and the reaction mixture heated to 60° C. After 1 hour at 60° C., 18-crown-6 (0.066 g, 0.25 mmol) is added. The solvent is removed under reduced pressure after 8 days at 60° C. and the residue dissolved by adding chloroform (60 ml), ethyl acetate (30 ml) and aqueous sodium hydroxide (1M, 50 ml). After separating the phases the aqueous phase is extracted with chloroform (3×25 ml). The combined organic layers are washed with water (2×50 ml) and dried ($MgSO_4$). The solvent is removed under reduced pressure to give 0.618 g (39%) of crude product. $^1$H NMR (60 MHz, $CDCl_3$): δ 1.67 (4 H, m, broad, $CH_2$—$CH_2$), 2.37 (4 H, m, broad, 2×$CH_2$—O), 5.77 (2H, s, O—$CH_2$—O).

EXAMPLE 23

Polymer from hexamethylene di(chloromethyl carbonate) and di-potassium terephthalate Potassium tert.butoxide (0.804 g, 7.16 mmol) is added to a solution of terephthalic acid (0.595 g, 3.58 mmol) in DMF (40 ml) at 20° C., under a dry $N_2$ atmosphere. Hexamethylene di(chloromethyl carbonate) prepared as described in Example 19 (1.00 g, 3.58 mmol) and 18-crown-6 (0.047 g, 0.179 mmol) are added to the resulting suspension and the reaction mixture heated to 60° C. The solvent is removed under reduced pressure after 6 days at 60° C. The residue is insoluble in dichloromethane and sodium hydroxide (1M), indicating the formation of a polymer.

EXAMPLE 24

Methylene di(3,3,-dimethoxypropionate)

Cesium 3,3-dimethoxypropionate (19.95 g, 75 mmol) is added to dry DMF (1l). Diiodomethane (10.04 g, 37.5 mmol) is added to the suspension and the reaction mixture is stirred for 2 days at 60° C. under a dry $N_2$ atmosphere. DMF is removed under reduced pressure (0.01 mmHg). Diethyl ether (500 ml) is added to the residue, which is then washed with saturated aqueous sodium hydrogen carbonate (250 ml). The aqueous layer is extracted with diethyl ether (5×75 ml). The combined ether extracts are washed with water (2×100 ml), dried ($MgSO_4$) and evaporated to give 7.1 g (72%) product. $^1$H NMR (300 MHz, $CDCl_3$): δ 2.61 ($CH_2$, d), 3.26 ($CH_3$, s), 4.76 (CH,t), 5.70 ($CH_2$, s). $^{13}$C NMR (300 MHz, $CDCl_3$): δ 38.52 ($CH_2$), 53.37 ($CH_3O$), 79.02 ($OCH_2O$), 168.32 (C=O).

EXAMPLE 25

Epoxy resin based on methylene bis[p-2,3-epoxy-1-propyloxy))benzoate] and an aliphatic polyamine A sample of methylene bis[p-(2,3-epoxy-1-propyloxy-)benzoate] prepared as described in Example 18 is blended with an equal weight of a commercial aliphatic polyamine curing agent. This mixture is used as an adhesive to adhere two glass plates together at room temperature. The resin is observed to have hardened and good bonding is obtained within 24 hours of mixing.

EXAMPLE 26

Aqueous polymer gel prepared by crosslinking an aqueous solution of poly(vinyl-alcohol) with methylene di(3,3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.8 by adding hydrochloric acid (18% solution). To this solution, 0.10 g (0.35 mmol) of methylene di(3,3-dimethoxypropionate) prepared as described in Example 24 is added, and the solution is well mixed. After 24 hours at room temperature the viscosity of the solution is higher than initially, and after 48 hours at room temperature the solution has formed a relatively strong gel. The gel is thoroughly washed with excess water for one day and stored under water to avoid drying. The water content of this gel is measured as being 98.5% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.3 by adding hydrochloric acid (18% solution). To this solution, 0.10 g (0.35 mmol) of methylene di(3,3-dimethoxypropionate) prepared as described in Example 24 is added, and the solution is well mixed. After 6 hours the solution has formed a gel and after 48 hours syneresis is observed. The gel is thoroughly washed with excess water for one day and stored under water to avoid drying. The water content for this gel is measured as being 95.5% (by volume).

(c) 5 g of an aqueous solution of poly(vinyl alcohol) (6.25 w % in water, 7.0 mmol with respect to monomer units, average M.W. 126 000, 98% hydrolyzed) is adjusted to pH=0.8 by adding hydrochloric acid (18% solution). To this solution is added 19.6 mg (0.07 mmol) of methylene di(3,3-dimethoxypropionate) prepared as described in Example 24 in 1 ml of water, and the solution is well mixed. After 3 hours at 50° C. the solution has formed a gel. The gel is thoroughly washed with excess water for one day and stored under water to avoid drying. The water content for this gel is estimated to be 98% (by volume).

(d) 5 g of an aqueous solution of poly(vinyl alcohol) (6.25 w % in water, 7.0 mmol with respect to monomer units, average M.W. 126 000, 98% hydrolyzed) is adjusted to pH=0.8 by adding hydrochloric acid (18% solution). To this solution 0.1 g (0.35 mmol) of methylene di(3,3-dimethoxypropionate) prepared as described in Example 24 is added, and the solution is well mixed. After 3 hours at 50° C. the solution has formed a gel. The gel is thoroughly washed with excess water for one day and stored under water to avoid drying. The water content for this gel is estimated to be 95% (by volume).

(e) 5 g of an aqueous solution of poly(vinyl alcohol) (6.25 w % in water, 7.0 mmol with respect to monomer units, average M.W. 126 000, 98% hydrolyzed) is adjusted to pH=0.8 by adding hydrochloric acid (18% solution). To this solution is added 19.6 mg (0.07 mmol) of methylene di(3, 3-dimethoxypropionate) prepared as described in Example 24 in 1 ml of water, and the solution is well mixed. After 40 minutes at 80° C. the solution has formed a gel. The gel is thoroughly washed with excess water for one day and stored under water to avoid drying. The water content for this gel is estimated to be 98% (by volume).

(f) 5 g of an aqueous solution of poly(vinyl alcohol) (6.25 w % in water, 7.0 mmol with respect to monomer units, average M.W. 126 000, 98% hydrolyzed) is adjusted to pH=0.8 by adding hydrochloric acid (18% solution). To this solution 0.1 g (0.35 mmol) of methylene di(3,3-dimethoxypropionate) prepared as described in Example 24 is added, and the solution is well mixed. After 40 minutes at 80° C. the solution has formed a gel. The gel is thoroughly washed with excess water for one day and stored under water to avoid drying. The water content for this gel is estimated to be 95% (by volume).

(g) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution is added 19.6 mg (0.07 mmol) of methylene di(3, 3-dimethoxypropionate) prepared as described in Example 24 in 1 ml of water, and the solution is well mixed. After 40 minutes at 80° C. the solution has formed a gel. The gel is thoroughly washed with excess water for one day and stored under water to avoid drying. The water content for this gel is estimated to be 98% (by volume).

(h) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution 0.1 g (0.35 mmol) of methylene di(3,3-dimethoxypropionate) prepared as described in Example 24 is added, and the solution is well mixed. After 40 minutes at 80° C. the solution has formed a gel. The gel is thoroughly washed with excess water for one day and stored under water avoid drying. The water content for this gel is estimated to be 95% (by volume).

EXAMPLE 27

Polymer gel containing chloramphenicol, prepared by radical polymerization of a water/DMSO (90:10) solution of the drug, acrylamide and methylene dimethacrylate AIBN (0.010 g, 0.061 mmol) is added to a solution of acrylamide (5.00 g, 70.34 mmol), methylene dimethacrylate prepared as described in Example 4(a) (0.250 g, 1.36 mmol) and chloramphenicol (0.051 g, 0.157 mmol) in water/DMSO(90:10, 20 ml) at 60° C. under a dry $N_2$ atmosphere, with good stirring. AIBN (0.010 g, 0.061 mmol) is again added after 1.5 hours. After a total of 3 hours the reaction mixture is cooled to 20° C. The reaction mixture then proves to be a soft gel. The gel does not dissolve in water, even after 7 days, whereas the corresponding acrylamide homopolymer is water-soluble.

EXAMPLE 28

Polymer gel containing testosterone, prepared by radical polymerization of a water/DMSO (90:10) solution of the drug, acrylamide and methylene diacrylate AIBN (0.010 g, 0.061 mmol) is added to a solution of acrylamide (5.00 g, 70.34 mmol), methylene diacrylate prepared as described in Example 4(b) (0.212 g, 1.36 mmol) and testosterone (0.050 g, 0.173 mmol) in water/DMSO (90:10, 20 ml) at 60° C. under a dry $N_2$ atmosphere, with good stirring. After 40 mins. the reaction mixture has turned into a gel. The reaction mixture is kept at 60° C. for a total of 2 hours to complete the reaction. Upon cooling to 20° C. the testosterone crystallizes in the gel. The gel does not dissolve in water, whereas the corresponding acrylamide homopolymer is water-soluble.

EXAMPLE 29

Polymer gel containing 5-fluorouracil, prepared by radical polymerization of a water/DMSO (14:1) solution of the drug, acrylamide and methylene diacrylate An aqueous solution of 5-fluorouracil (5.00 ml, 250 mg/10 ml, 0.961 mmol) is added to a solution of acrylamide (5.00 g, 70.34 mmol) and methylene diacrylate prepared as described in Example 4(b) (0.212 g, 1.36 mmol) in water/DMSO (90:10, 10 ml) at 60° C. under a dry $N_2$ atmosphere, with good stirring. AIBN (0.010 g, 0.061 mmol) is then added and after 35 mins. the reaction mixture has turned into a gel. The reaction mixture is kept at 60° C. for a total of 2 hours to complete the reaction. The gel does not dissolve in water, whereas the corresponding acrylamide homopolymer is water-soluble.

EXAMPLE 30

Polymer gel containing sulfadiazine, prepared by suspending the drug an aqueous solution of poly(vinyl alcohol) subsequently crosslinked with methylene di(3,3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 19.6 mg (0.07 mmol) of methylene di(3,3-dimethoxypropionate) prepared as described in Example 24 in 1 ml of water and 0.20 g (0.8 mmol) of sulfadiazine, and the dispersion is well mixed. After 40 minutes at 80° C. the solution has formed a gel with the powder suspended in it. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 0.1 g (0.35 mmol) of methylene di(3,3-dimethoxypropionate) prepared as described in Example 24 and 0.20 g (0.8 mmol) of sulfadiazine, and the suspension is well mixed. After 40 minutes at 80° C. the polymer has formed a gel with the powder suspended in it. The gel is thoroughly washed with excess water for one day and stored under water to avoid drying. The water content for this gel is estimated to be 95% (by volume).

EXAMPLE 31

Polymer gel containing progesterone, prepared by suspending the drug in an aqueous solution of poly(vinyl alcohol) subsequently crosslinked with methylene di(3,3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 19.6 mg (0.07 mmol) of methylene di(3,3-dimethoxypropionate) prepared as described in Example 24 in 1 ml of water and 0.07 g (0.2 mmol) of progesterone, and the dispersion is well mixed. After 40 minutes at 80° C. the polymer has formed a gel with the powder suspended in it. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 0.1 g (0.35 mmol) of methylene di(3,3-dimethoxypropionate) prepared as described in Example 24 and 0.07 g (0.2 mmol) of progesterone, and the suspension is well mixed. After 40 minutes at 80° C. the polymer has formed a gel with the powder suspended in it. The gel is thoroughly washed with excess water for one day and stored under water to avoid drying. The water content for this gel is estimated to be 95% (by volume).

EXAMPLE 32

Polymer gel containing 5-fluorouracil, prepared by dissolving the drug in an aqueous solution of poly(vinyl alcohol) subsequently crosslinked with methylene di(3,3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 19.6 mg (0.07 mmol) of methylene di(3,3-dimethoxypropionate) prepared as described in Example 24 in 1 ml of water and 13 mg (0.1 mmol) of 5-fluorouracil dissolved in 0.5 ml water, and the solution is well mixed. After 40 minutes at 80° C. the solution has formed a gel. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 0.1 g (0.35 mmol) of methylene di(3,3-dimethoxypropionate) prepared as described in Example 24 and 13 mg (0.1 mmol) of 5-fluorouracil dissolved in 0.5 ml water, and the solution is well mixed. After 40 minutes at 80° C. the solution has formed a gel. The gel is thoroughly washed with excess water for one day and stored under water to avoid drying. The water content for this gel is estimated to be 95% (by volume).

EXAMPLE 33

Polymer gel containing Omnipaque™, prepared by dissolving the diagnostic aid in an aqueous solution of poly(vinyl alcohol) subsequently crosslinked with methylene di(3,3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 19.6 mg (0.07 mmol) of methylene di(3,3-dimethoxypropionate) prepared as described in Example 24 in 1 ml of water and 1 ml of Omnipaque™ (300 mgI/ml), and the solution is well mixed. After 40 minutes at 80° C. the solution has formed a gel. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 0.1 g (0.35 mmol) of methylene di (3,3-dimethoxypropionate) prepared as described in Example 24 and 1 ml of Omnipaque™ (300 mgI/ml), and the solution is well mixed. After 40 minutes at 80° C. the solution has formed a gel. The gel is thoroughly washed with excess water for one day and stored under water to avoid drying. The water content for this gel is estimated to be 95% (by volume).

EXAMPLE 34

Polymer gel containing magnetic starch microspheres, prepared by suspending the material in an aqueous solution of poly(vinyl alcohol) subsequently crosslinked with methylene di(3,3-dimethoxypropionate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 19.6 mg (0.07 mmol) of methylene di(3,3-dimethoxypropionate) prepared as described in Example 24 in 1 ml of water and 0.5 ml of a suspension containing magnetic starch microspheres prepared as described in WO 85/02772 (Schröder) (7.5 mg Fe/ml, 0.9% NaCl, 0.5% glycerol), and the suspension is well mixed. After 40 minutes at 80° C. the polymer has formed a gel with the magnetic material suspended in it. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution are added 0.1 g (0.35 mmol) of methylene di(3,3-dimethoxypropionate) prepared as described in Example 24 and 0.5 ml of a suspension containing magnetic starch microspheres prepared as described in WO 85/02772 (Schroder) (7.5 mg Fe/ml, 0.9% NaCl, 0.5% glycerol), and the suspension is well mixed. After 40 minutes at 80° C. the polymer has formed a gel with the magnetic material suspended in it. The gel is thoroughly washed with excess water for one day and stored under water to avoid drying. The water content for this gel is estimated to be 97% (by volume).

EXAMPLE 35

Homopolymerisation of methylene dimethacrylate 0.5 g (2.7 mmol) of methylene dimethacrylate prepared as described in Example 4(a) is blended with 2.5 mg (15 μmol) of AIBN. After 2 hours at 70° C. the monomer has formed a hard solid. This polymer is insoluble, indicating that its structure is a tightly crosslinked network.

EXAMPLE 36

Homopolymerisation of (2-methacryloyloxy)ethyl methacryloyloxymethyl carbonate 0.4340 g (1.6 mmol) of (2-methacryloyloxy)ethyl methacryloyloxymethyl carbonate prepared as described in Example 4(d) is blended with 22.0 mg (13.2 μmol) of AIBN. After 2 hours at 70° C. the monomer has formed a hard solid. This polymer is insoluble, indicating that its structure is a tightly crosslinked network.

EXAMPLE 37

Emulsion copolymerisation of methylene dimethacrylate and methyl methacrylate 50 ml of a 1% wt/vol solution of sodium dodecyl sulphate in water is pre-heated to 60° C. under a nitrogen atmosphere. 0.20 g (1.09 mmol) of methylene dimethacrylate prepared as described in Example 4(a) and 9.80 g (0.098 mol) of methyl methacrylate monomer are added under vigorous stirring. The polymerisation is initiated with a metabisulphite/persulphate redox system comprising 1.6 mg (7.2 μmol) potassium metabisulphite and 0.08 mg (0.3 μmol) potassium persulphate. The polymerisation is permitted to proceed for 8 hours before cooling to room temperature. The resultant emulsion has a solids content of 11.1% which corresponds to a degree of conversion of 66%. The recovered polymer is not soluble in THF, a good solvent for poly(methyl methacrylate), indicating that the polymer is crosslinked.

EXAMPLE 38

Emulsion copolymerisation of methylene dimethacrylate and styrene 50 ml of a 1% wt/vol solution of sodium dodecyl sulphate in water is pre-heated to 60° C. under a nitrogen atmosphere. 0.20 g (1.09 mmol) of methylene dimethacrylate prepared as described in Example 4(a) and 9.80 g (0.094 mol) styrene monomer are added under vigorous stirring. The polymerisation is initiated with a metabisulphite/persulphate redox system comprising 1.6 mg (7.2 μmol) potassium metabisulphite and 0.08 mg (0.3 μmol) potassium persulphate. The polymerisation is permitted to proceed for 8 hours before cooling to room temperature. The resultant emulsion has a solids content of 11.2% which corresponds to a degree of conversion of 68%. The recovered polymer is not soluble in THF, a good solvent for polystyrene, indicating that the polymer is crosslinked.

EXAMPLE 39

Emulsion copolymerisation of acryloyloxymethyl 4-acryloyloxybutyl carbonate and methyl methacrylate 50 ml of a 1% wt/vol solution of sodium dodecyl sulphate in water is pre-heated to 60° C. under a nitrogen atmosphere. 0.20 g (0.74 mmol) of acryloyloxymethyl 4-acryloyloxybutyl carbonate prepared as described in Example 4(k) and 9.80 g (0.098 mol) of methyl methacrylate monomer are added under vigorous stirring. The polymerisation is initiated with a metabisulphite/persulphate redox system comprising 1.6 mg (7.2 μmol) potassium metabisulphite and 0.08 mg (0.3 μmol) potassium persulphate. The polymerisation is permitted to proceed for 8 hours before cooling to room temperature. The resultant emulsion has a solids content of 11.2% which corresponds to a degree of conversion of 67%. The recovered polymer is not soluble in THF, a good solvent for poly(methyl methacrylate), indicating that the polymer is crosslinked.

EXAMPLE 40

Emulsion copolymerisation of acryloyloxymethyl 4-acryloyloxybutyl carbonate and styrene 50 ml of a 1% wt/vol solution of sodium dodecyl sulphate in water is pre-heated to 60° C. under a nitrogen atmosphere. 0.20 g (0.74 mmol) of acryloyloxymethyl 4-acryloyloxybutyl carbonate prepared as described in Example 4(k) and 9.80 g (0.094 mol) of styrene monomer are added under vigorous stirring. The polymerisation is initiated with a metabisulphite/persulphate redox system comprising 1.6 mg (7.2 μmol) potassium metabisulphite and 0.08 mg (0.3 μmol) potassium persulphate. The polymerisation is permitted to proceed for 8 hours before cooling to room temperature. The resultant emulsion has a solids content of 12% which corresponds to a degree of conversion of 72%. The recovered polymer is not soluble in THF, a good solvent for polystyrene, indicating that the polymer is crosslinked.

EXAMPLE 41

Polymer gel containing magnetic starch microspheres prepared by radical polymerization of a water/DMSO (90:10) suspension of magnetic starch microspheres acrylamide and 1-acryloyloxyethyl 4-acryloyloxybutyl carbonate An aqueous suspension of magnetic starch microspheres prepared as described in WO 85/02722 (Schröder) (0.50 ml from a solution containing 7.5 mg Fe/ml, 0.9% NaCl and 0.5% glycerol) is added to a solution of acrylamide (5.00 g, 70.34 mmol) and 1-acryloyloxyethyl 4-acryloyloxybutyl carbonate prepared as described in Example 4(l) (0.359 g, 1.36 mmol) in water/DMSO (90:10, 10 ml) at 60° C. under a dry $N_2$ atmosphere, with good stirring. AIBN, (0.010 g, 0.061 mmol) is then added and after approximately 40 minutes the reaction mixture has turned into a gel. The reaction mixture is kept at 60° C. for a total of 2 hours to complete the reaction. The gel does not dissolve in water, whereas the corresponding acrylamide homopolymer is water-soluble.

EXAMPLE 42

Polymer from hexamethylene di(chloromethyl carbonate) and 2,3,5,6-tetraiodoterephthalic acid A solution of hexamethylene di(chloromethyl carbonate) prepared as described in Example 19 (0.61 g, 2 mmol) in dry DMF (2 ml) is added dropwise to a suspension of di-potassium 2,3,5,6-tetraiodoterephthalate (1.49 g, 2 mmol) and 18-crown-6 (0.03, 0.1 mmol) in dry dimethylformamide (18 ml) under an $N_2$ atmosphere. After 4 days at 60° C. the solvent is removed under reduced pressure (0.5 mm Hg). The residue is dissolved in chloroform (400 ml) and washed with saturated aqueous sodium hydrogen carbonate (3×200 ml) and water (2×200 ml). The organic phase is dried ($MgSO_4$) and evaporated to give 1.16 g of product. $^1H$ NMR (300 MHz): δ 1.38–1.45 (m, area=0.24), 1.65–1.76 (m, area=0.24), 4.18–4.25 (m, area=0.23), 5.73 (s, area=0.01), 5.99 (s, area=0.21). The area ratio between the signal at δ 5.73 from the α-chloromethylene group of the aliphatic monomer and the signal at δ 5.99 from the methylene diester groups confirms that a polymer is formed.

EXAMPLE 43

Covalent attachment of MCPA to 2-hydroxyethyl methacrylate polymer crosslinked with 0.5% 2-methacryloyloxyethyl methacryloyloxyethyl carbonate The gel described in Example 10 (2.0 g) is swelled in 20 ml dry DMSO. The gel suspension is added a solution of 2-methyl- 4-chloro-phenoxy acetic acid (MCPA) (2.0 g, 10 mmol), N-ethyl-N'-(3-(N"-dimethylamino) propyl) carbodiimide and 4-pyrrolidinopyridine (160 mg, 1 mmol) in 30 ml dry DMSO, under a dry nitrogen atmosphere. The suspension is shaken for 24 hours at room temperature, and the gel is washed with DMSO and finally water and dried in vacuo to yield the product. The resulting water suspensible gel contains the highly water soluble weed killer MCPA covalently attached to the gel and provides sustained release of the agrochemical.

EXAMPLE 44

Covalent attachment of 5-acetylamino-3-(N-methylacetylamino)- 2,4,6-triiodobenzoic acid (Isopaque) to 2-hydroxyethyl methacrylate polymer crosslinked with 0.5% 2-methacryloyloxyethyl methacryloyloxymethyl carbonate (a) The Isopaque amide of β-alanine-O-benzyl ester Potassium carbonate (0.69, 5 mmol) is added to a solution of H-β-alanine-O-benzyl ester (1.76 g, 5 mmol) in dry dimethylformamide (50 ml) at 0° C. After 10 minutes at ambient temperature, 5-acetylamino-3 -(N-methylacetylamino)-2,4,6-triiodobenzoyl chloride (Isopaque acid chloride) (3.23 g, 5 mmol) dissolved in dry dimethylformamide (20 ml) is added dropwise to the suspension at 0° C. under a nitrogen atmosphere. The reaction mixture is heated to 50° C. After 24 hours the solvent is removed under reduced pressure and chloroform (500 ml) and water (200 ml) are added. The organic phase is washed with saturated aqueous sodium hydrogen carbonate (100 ml), 0.01M HCl (100 ml) and water (2×100 ml). After drying of the organic phase evaporation of the solvent gives 3.10 g product (79%). $^1$H NMR (300 MHz): δ 1.72–1.83 (m), 2.15–2.23 (m), 2.72–2.81 (m), 3.0–3.09 (m), 3.67–3.78 (m), 5.05–5.20 (m), 6.6–7.0 (m), 7.31–7.35 (m), 8.5–8.9 (m).

(b) Debenzylation of the Isopaque amide of β-alanine-O-benzyl ester

The Isopaque amide of β-alanine-O-benzyl ester prepared in (a) above (1.578 g, 2 mmol) is dissolved in dry methanol (50 ml). Palladium on charcoal (10%, 0.4 g) is added in one portion with stirring of the reaction mixture. Hydrogen gas is bubbled into the solution for two hours, and then the reaction mixture is stirred for a further 2 hours. Filtration and evaporation of the solvent yield a yellow residue, which is purified on a weakly cationic ion exchanger to yield the product.

(c) Attachment of 5-acetylamino-3-(N-methylacetylamino)- 2,4,6-triiodobenzoic acid (Isopaque) to polymer gel The carboxylic acid from (b) above is attached to the gel described in Example 10 using the method described in Example 43.

EXAMPLE 45

Methylene di(3-methoxypropenoate)

Methylene di(3,3-dimethoxypropionate) prepared as described in Example 24 (14.01 g, 50 mmol) and a catalytic amount of p-toluene sulfonic acid is added to toluene (250 ml). The methanol is removed by warming the reaction under an $N_2$ atmosphere. When the reaction is complete the toluene is distilled off under reduced pressure. Diethyl ether (250 ml) is added and the mixture is washed with saturated aqueous sodium hydrogen carbonate (5×50 ml) and water (3×50 ml). The organic layer is dried (MgSO$_4$) before evaporation to give 8.52 g (79%) product.

EXAMPLE 46

Aqueous polymer gel prepared by crosslinking an aqueous solution of poly(vinyl alcohol) with methylene di(3-methoxypropenoate)

(a) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution is added 55 mg (0.23 mmol) of methylene di(3-methoxypropenoate) prepared as described in Example 45 in 1 ml of 50:50 dioxane/water, and the solution is well mixed. After 40 minutes at 80° C. the solution has formed a gel. The gel is thoroughly washed with excess water for one day and stored under water to avoid drying. The water content for this gel is estimated to be 98% (by volume).

(b) 5 g of an aqueous solution of poly(vinyl alcohol) (6.25 w % in water, 7.0 mmol with respect to monomer units, average M.W. 126 000, 98% hydrolyzed) is adjusted to pH=0.4 by adding hydrochloric acid (18% solution). To this solution is added 110 mg (0.56 mmol) of methylene di(3-methoxypropenoate) prepared as described in Example 45 in 2 ml of 50:50 dioxane/water, and the solution is well mixed. After 40 minutes at 80° C. the solution has formed a gel. The gel is thoroughly washed with excess water for one day and stored under water to avoid drying. The water content for this gel is estimated to be 97% (by volume).

EXAMPLE 47

(a) Methylene bis(10-undecenoate)

10-Undecylenic acid (12.75 g, 75 mmol) is dissolved in 100 ml water. Cesium carbonate (13.04 g, 40 mmol) is added to the mixture. The water is removed under reduced pressure and the salt dried for 2 hours in vacuo. The cesium salt is mixed with 150 ml DMF and diiodomethane is added to the solution. The reaction is stirred for 3 days at 60° C. under an $N_2$ atmosphere. DMF is then removed under reduced pressure. The residue is purified through silica gel with hexane/ethyl acetate (8:2) as eluant. The solvent is evaporated to give 7.18 g (54%) product. $^1$H NMR (300 MHz, CDCl$_3$): δ 1.2–1.4 (10×CH$_2$, m), 1.6 (2×CH$_2$, m), 2.0 (2×CH$_2$, m), 2.19 (2×CH$_2$, t), 4.9 (2×H$_2$ C═, m), 5.88 (O—CH$_2$—O, s), 5.9 (2×HC═, m). $^{13}$C NMR (300 MHz, CDCl$_3$): δ 24.92–33.98 (8×CH$_2$), 79.04 (O—CH$_2$—O), 114.18 (═CH$_2$), 139.11 (═CH), 172.48 (C═O).

(b) Methylene bis(10,11-epoxyundecanoate)

Methylene bis(10-undecenoate) (8.8 g, 25 mmol) is added under an $N_2$ atmosphere to methylene chloride and cooled to 0° C. Metachloroperbenzoic acid 55% (15.75 g, 50 mmol) is added to methylene chloride (150 ml) and the organic layer is separated and dried (MgSO$_4$). The metachloroperbenzoic acid is then added dropwise to the diester. After completed addition the temperature is increased to 25° C. After 5 hours the reaction is complete. The mixture is washed with saturated aqueous sodium sulphite (75 ml) and saturated aqueous sodium hydrogen carbonate (2×75 ml). The organic layer is purified on neutral aluminium oxide. The solvent is removed under reduced pressure to yield 8.45 g (82%) product. $^1$HNMR (300 MHz, CDCl$_3$): δ 1.2–1.7(14×CH$_2$, m), 2.35(2×CH$_2$CO,t), 2.45 (2×CH,q), 2.75 (2×CH,q), 2.90 (2×CH,m), 5.75 (O—CH$_2$—O). $^{13}$C NMR (300 MHz, CDCl$_3$): δ 24.58 (CH$_2$), 25.99 (CH$_2$), 28.94 (CH$_2$), 29.09 (CH$_2$), 29.32 (2×CH$_2$), 32.45 (CH$_2$), 33.92 (CH$_2$), 47.06 (CH$_2$—O), 52.36 (CH—O), 79.06 (O—CH$_2$—O), 172.2 (C═O).

EXAMPLE 48

(a) Methylene dibenzyloxyacetate

Benzyloxyacetic acid (49.8 g, 300 mmol) is dissolved in a 500 ml mixture of water and MeOH (60:40), and cesium carbonate (48.9 g, 150 mmol) is added to the solution. The solvent is evaporated under reduced pressure and residual water is removed azeotropically with benzene. The salt is dissolved in 1500 ml DMF and diiodomethane (40.2 g, 150 mmol) is added to the solution. The reaction mixture is stirred for 3 days at 60° C. under an N₂ atmosphere. The DMF is removed under reduced pressure and the residue is dissolved in ether (250 ml) and washed with saturated aqueous sodium hydrogen carbonate (250 ml) and water (3×75 ml) before drying (MgSO₄). The solvent is evaporated and the residue is purified through silica gel with hexane/ethyl acetate (7:3) as eluant to give 23.6 g (46%) product. $^1$H NMR (300 MHz, CDCl₃): δ 4.1 (2×CH₂, s), 4.6 (2×CH₂, s), 5.9 (O—CH₂—O, s), 7.35 (2 ×C₆H₅, m).
(b) Methylene dihydroxyacetate Methylene dibenzyloxyacetate (0.52 g, 1.5 mmol) and Pd/C (100 mg, 10%) are added to dry ethanol (100 ml). Hydrogen (1 atm) is introduced and the reaction is complete after 16 hours at room temperature, whereupon the reaction mixture is filtered and the solvent is evaporated under reduced pressure (0.01 mmHg) to yield 0.23 g (95%) product. $^1$H NMR (200 MHz, MeOH): δ 4.2 (CH₂, s), 4.9 (OH), 5.9 (OCH₂, s). The product may be used to form polyesters with di- or poly-acids and to form polyurethanes with isocyanates.

EXAMPLE 49

Homopolymerisation of methylene diepoxypropionate

Anhydrous tert.butylhydroperoxide (3.3 ml, 3M) and BuLi (6.7 ml, 1.5M) are dissolved in 30 ml cold (−78° C.) THF. The solution is stirred for 5 minutes before adding methylene diacrylate (0.78 g, 5 mmol). The reaction is performed under N₂ atmosphere for 1 hour. The cold mixture is filtered through neutral aluminium oxide and evaporated to yield a transparent polymer. The solubility properties of the product indicate that it is a polymer.

EXAMPLE 50

Homopolymerisation of 1-acryloyloxyethyl 4-acryoyloxybutyl carbonate 348.2 mg (1.22 mmol) of 1-acryloyloxyethyl 4-acryoyloxybutyl carbonate prepared as described in Example 4(l) is blended with 1.7 mg (10.2 μmol) AIBN. After 2 hours at 70° C. the monomer has formed a hard solid. This polymer is insoluble, indicating that its structure is a tightly crosslinked network.

EXAMPLE 51

Epoxy resin based on methylene bis(10,11-epoxyundecanoate) and an aliphatic polyamine A sample of methylene bis(10,11-epoxyundecanoate) prepared as described in Example 47 is blended with an equal weight of a commercial aliphatic polyamine curing agent. This mixture is cured on the surface of a glass plate at 70° C. The resin is observed to have hardened and good bonding is obtained within 2 hours of mixing.

EXAMPLE 52

Polymer from 1,6-diisocyanatohexane and methylene di(p-hydroxybenzoate)

1,6-Diisocyanatohexane (0.927 g, 5.51 mmol) is added to a solution of methylene di(p-hydroxybenzoate) prepared as described in Example 4(o) (1.588 g, 5.51 mmol) in DMF (15 ml) under a dry N₂ atmosphere. The reaction mixture is heated to 100° C. for 3 days before the solvent is removed under reduced pressure at 50° C. Upon cooling to 20° C. the product turns into a rubber-like material which is practically insoluble in a 1:1 mixture of chloroform and DMSO, indicating formation of a polymer.

EXAMPLE 53

Characterisation of the size of the polymers made in Examples 37, 38, 39 and 40

The characterisations are performed on a Malvern PS/MW 4700 using Buccard cells. Each sample is diluted until an opaque solution forms and is attempered to 25° C. prior to analysis. Viscosity of water=0.891 cP is used, and instrument settings are: Light Power=70 mW, PM-aperture= 200 m, Scattering angle=90°, Mode=Manual, Serial Configuration, Sample time=4 s, Experimental duration=90 s, Calculus mode= model independent, fit error minimized. To obtain results for the mass distribution a "Particle Refractive Index"=1.45 is used. Each sample is analysed in triplicate.

Mass mean particle hydrodynamic diameter (Dh) and distribution standard deviation (SD-distribution) for each sample are shown on the following Table. Experimental SD is shown in brackets.

| Example | Dh | SD-distribution |
|---|---|---|
| 37 | 57.5 (±1.5) nm | 11.2 (±1.7) nm |
| 38 | 58.7 (±0.9) nm | 12.1 (±1.3) nm |
| 39 | 56.7 (±0.7) nm | 16.6 (±1.2) nm |
| 40 | 62.1 (±1.6) nm | 14.0 (±2.6) nm |

EXAMPLE 54

(a) Enzyme-catalyzed hydrolysis of acrylamide polymer crosslinked with 2% acryloyloxymethyl 4-acryloyloxybutyl carbonate 432 mg samples of the polymer described in Example 12 and 50 ml 0.9% NaCl (Sterile, Hydro Pharma) are added to each of two reaction vials. To one of the vials is also added 1000 μl esterase (Sigma, E-2138, 2530 U). The pH within each vial is kept constant at 8.4 by adding 0.10M NaOH. By recording the consumption of NaOH the rates of hydrolysis are calculated. During 21 hours, hydrolysis of the polymer with esterase is found to be 8.5 times faster than the control without esterase.

(b) Enzyme-catalyzed hydrolysis of acrylamide polymer crosslinked with 2% methylene dimethacrylate compared with control polyester To one vial are added 500 mg acrylamide polymer crosslinked with 2% methylene dimethacrylate prepared according to the method of Example 5(a), 40 ml (0.16 M, pH 7.4) PBS (phosphate buffer) and 800 μl esterase (Sigma, E-2138, 2024 U).

As a control 500 mg acrylamide polymer crosslinked with 2% ethylene dimethacrylate (prepared according to the method of Example 5(a) but using ethylene dimethacrylate instead of methylene dimethacrylate), 40 ml (0.16M, pH 7.4) PBS (phosphate buffer) and 800 μl esterase (Sigma, E-2138, 2024 U) are added to a second vial.

For the control polyester, pH of the buffer decreases from 7.1 to 6.9 during 200 hours, while pH in the buffer solution containing acrylamide polymer crosslinked with methylene dimethacrylate decreases from 7.1 to 6.4 during 24 hours, indicating that the acid metabolites are formed much faster for methylene dimethacrylate polymer than for the control polyester.

EXAMPLE 55

Polymer from starch crosslinked with methylene bis(10,11-epoxyundecanoate)

Titanum (IV) isopropoxide (1.11 g, 3.9 mmol) is added to a solution of methylene bis(10,11-epoxyundecanoate) prepared as described in Example 47 (1.0 g, 2.6 mmol) and starch (1.0 g) in dry DMSO (50 ml). The reaction mixture is stirred for 4 hours at ambient temperature. Chloroform/ether (250 ml, 1:1) is added, the oily material is dissolved in water and extracted with chloroform (2×50 ml). The aqueous phase is subjected to dialysis or gel filtration to furnish the polymer.

EXAMPLE 56

Polymer from dextran 70000 crosslinked with methylene bis (10,11-epoxyundecanoate)

Titanum (IV) isoproxide (1.11 g, 3.9 mmol) is added to a solution of methylene bis(10,11-epoxyundecanoate) prepared as described in Example 47 (1.0 g, 2.6 mmol) and dextran 70,000 in dry DMSO (50 ml). The reaction mixture is stirred for 4 hours at ambient temperature. Chloroform/ether (250 ml, 1:1) is added, the oily material is dissolved in water and extracted with chloroform (2×50 ml). The aqueous phase is subjected to dialysis or gel filtration to furnish the polymer.

EXAMPLE 57

Polymer from protein crosslinked with methylene bis(10, 11-epoxyundecanoate)

Methylene bis(10,11-epoxyundecanoate) prepared as described in Example 47 (1.0 g, 2.6 mmol) is added to a solution of human serum albumin (1.0 g) in buffer (50 ml). The reaction mixture is stirred at ambient temperature overnight and evaporated. The polymer is washed several times with tetrahydrofuran and dried under reduced pressure.

We claim:

1. Biodegradable polymers comprising diester units of the formula (I)

where $R^1$ and $R^2$ each represents a hydrogen atom or a carbon-attached monovalent organic group or $R^1$ and $R^2$ together form a carbon-attached divalent organic group.

2. Biodegradable polymers as claimed in claim 1 in which the diester units have the formula (II)

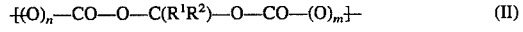

where m and n, which may be the same or different, are 0 or 1.

3. Biodegradable polymers as claimed in claim 2 in which the diester units have the formula (III)

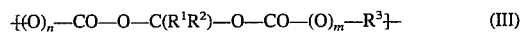

where $R^3$ is a carbon-attached divalent organic grouping.

4. Biodegradable polymers as claimed in claim 2 wherein n is 0 and m is 0 or 1.

5. Biodegradable polymers as claimed in claim 1 in which $R^1$ and $R^2$ are each hydrogen or a carbon-attached hydrocarbyl or heterocyclic group.

6. Biodegradable polymers as claimed in claim 5 in which $R^1$ and $R^2$ are each hydrogen or an aliphatic group having up to 10 carbon atoms, a cycloalkyl group having up to 10 carbon atoms, an araliphatic group having up to 20 carbon atoms, an aryl group having up to 20 carbon atoms or a heterocyclic group having up to 20 carbon atoms and one or more heteroatoms selected from the group consisting of O, S and N.

7. Biodegradable polymers as claimed in claim 1 which are block or graft copolymers.

8. Biodegradable polymers as claimed in claim 1 in the form of surgical implants, soft tissue prostheses, sponges, films, wound dressings, flexible sheets, containers and delayed release formulations for drugs and agricultural chemicals, particulate imaging agents or plasticisers.

9. Biodegradable polymers as claimed in claim 1 comprising a plurality of polymer chains cross-linked by diester units of formula (I).

10. Biodegradable polymers as claimed in claim 3 wherein n is 0 and m is 0 or 1.

11. Biodegradable polymers as claimed in claim 3 wherein $R^1$ and $R^2$ are each hydrogen or a carbon-attached hydrocarbyl or heterocyclic group.

12. Biodegradable polymers as claimed in claim 3 in which $R^3$ is selected from the group consisting of alkylene and alkenylene groups having up to 20 carbon atoms, cycloalkylene groups having up to 10 carbon atoms, aralkylene groups having up to 20 carbon atoms, arylene groups having up to 20 carbon atoms, heterocyclic groups having up to 20 carbon atoms and one or more heteroatoms selected from the group consisting of O, S and N, and any of the preceding groups interrupted by oxygen, substituted by oxygen or interrupted and substituted by oxygen.

13. Biodegradable polymers as claimed in claim 1 which are linear polymers.

* * * * *